(12) United States Patent
Publicover et al.

(10) Patent No.: US 7,514,938 B2
(45) Date of Patent: Apr. 7, 2009

(54) DIELECTRIC RELAXATION SPECTROSCOPY APPARATUS AND METHODS OF USE

(75) Inventors: Nelson George Publicover, Reno, NV (US); Craig A. Vincze, Reno, NV (US)

(73) Assignee: Board of Regents of the University and College System of Nevada, on Behalf of the University of Nevada, Reno, Reno, NV (US)

( * ) Notice: Subject to any disclaimer, the term of this patent is extended or adjusted under 35 U.S.C. 154(b) by 0 days.

(21) Appl. No.: 11/127,632

(22) Filed: May 11, 2005

(65) Prior Publication Data

US 2005/0266396 A1    Dec. 1, 2005

Related U.S. Application Data

(60) Provisional application No. 60/570,367, filed on May 11, 2004.

(51) Int. Cl.
G01R 27/26 (2006.01)
G01N 33/53 (2006.01)

(52) U.S. Cl. .................. 324/663; 324/452; 324/464; 435/7.1; 435/287.1

(58) Field of Classification Search .................. 324/663, 324/552, 452
See application file for complete search history.

(56) References Cited

U.S. PATENT DOCUMENTS

| | | | |
|---|---|---|---|
| 5,150,036 A * | 9/1992 | Pourprix | ..................... 324/71.4 |
| 5,869,973 A | 2/1999 | Nosov | |
| 6,169,394 B1 * | 1/2001 | Frazier et al. | ............... 324/71.4 |
| 6,287,776 B1 | 9/2001 | Hefti | |
| 6,287,874 B1 | 9/2001 | Hefti | |
| 6,340,568 B2 | 1/2002 | Hefti | |
| 6,368,795 B1 | 4/2002 | Hefti | |
| 6,395,480 B1 | 5/2002 | Hefti | |
| 6,485,905 B2 | 11/2002 | Hefti | |
| 6,566,079 B2 | 5/2003 | Hefti | |
| 6,801,029 B2 | 10/2004 | Van Der Weide et al. | |

(Continued)

FOREIGN PATENT DOCUMENTS

WO    WO 8903095 A1 *    5/1987
WO    WO 9739343 A1 *    10/1997

OTHER PUBLICATIONS

Asami, "The Scanning Dielectric Microscope," *Meas. Sci. Technol.*, vol. 5, 589-592 (1994).

(Continued)

*Primary Examiner*—Vincent Q Nguyen
*Assistant Examiner*—John Zhu
(74) *Attorney, Agent, or Firm*—University of Nevada, Reno/DRI Technology Transfer Office; Ryan A. Heck, J.D.

(57) ABSTRACT

Methods and apparatus for measuring the dielectric relaxation properties of a sample are disclosed. Methods are disclosed for amplifying or controlling the dielectric relaxation properties of a sample by adding particles, such as functionally coated particles. In certain methods, the particles amplify or control the dielectric relaxation properties of the sample by interacting with counter ions in the sample. In some embodiments, the methods use a dielectric relaxation spectroscopy apparatus with remote electrodes.

18 Claims, 25 Drawing Sheets

U.S. PATENT DOCUMENTS

| | | | | |
|---|---|---|---|---|
| 6,810,732 | B2* | 11/2004 | Shon .......................... | 73/304 R |
| 6,828,800 | B2* | 12/2004 | Reich et al. .................. | 324/658 |
| 2003/0054569 | A1* | 3/2003 | Cheng et al. ................ | 436/516 |
| 2003/0102854 | A1* | 6/2003 | Gascoyne et al. ........... | 324/71.4 |
| 2003/0119057 | A1* | 6/2003 | Gascoyne et al. ............ | 435/7.1 |
| 2003/0175994 | A1* | 9/2003 | Palti ............................ | 436/533 |
| 2004/0108857 | A1* | 6/2004 | Jarski et al. ................. | 324/464 |
| 2004/0171092 | A1* | 9/2004 | Harris et al. ................ | 435/7.92 |

OTHER PUBLICATIONS

Bataillard, et al., "Direct Detection of Immunospecies by Capacitance Measurements," *Anal. Chem.*, vol. 60, 2374-2379 (1988).

Chonde, et al., "Dielectric Spectroscopy of High-Solids, Styrene-Butadiene Latex Dispersions," *Journal of Colloid and Interface Science*, vol. 186, 248-253 (1997).

Fixman, et al., "Spherical Macroions in Strong Fields," *Macromolecules*, vol. 16, 685-699 (1983).

Grosse, et al., "Broad Frequency Range Study of the Dielectric Properties of Suspensions of Colloidial Polystyrene Particles in Aqueous Electrolyte Solutions," *Journal of Colloid and Interface Science*, vol. 205, 26-41 (1998).

Pei, et al., "Amplification of Antigen-Antibody Interactions Based on Biotin Labeled Protien-Streptavidin Network Complex Using Impedance Spectroscopy," *Biosensors & Bioelectronics*, vol. 16, 355-361 (2001).

Smith, et al., "Dielectric Relaxation Spectroscopy and Some Applications in the Pharmaceutical Science," *Journal of Pharmaceutical Sciences*, vol. 84, No. 9, 1029-1044 (Sep. 1995).

Suherman, at al., "Development of a Remote Electrode System for Monitoring the Water Content of Materials inside a Glass Vial," *Pharmaceutical Research*, vol. 19, No. 3, 337-344 (Mar. 2002).

Vincze, "Remote Electrode, Sensor Platform Using Dielectric Relaxation of Nanoparticle Counter Ions," *Ph.D. dissertation*, (Aug. 2004).

Williams, "Dielectric and Electrical Properties of Materials," *Dielectrics Newsletter*, 1-8 (Mar. 1994).

\* cited by examiner

No applied field

E

DIELECTRIC RELAXATION SPECTROSCOPY APPARATUS AND METHODS OF USE

CROSS REFERENCE TO RELATED APPLICATION

This application claims the benefit of, and incorporates by reference, U.S. Provisional Patent Application No. 60/570,367, filed May 11, 2004.

FIELD

This invention relates to dielectric relaxation spectroscopy ("DRS") apparatus and methods of use. Specifically, certain disclosed examples provide DRS apparatus with remote electrodes or particles. Certain disclosed DRS apparatus and methods can be used as sensors, including biosensors.

BACKGROUND

Dielectric relaxation spectroscopy (DRS) is attractive because of its ability to probe particle properties and interactions without the use of chemically attached dyes, labels, or markers. However, the widespread use of DRS as a sensor platform has been limited, in part, because of problems associated with interfacial polarization and surface regeneration of electrodes.

Most DRS and impedance spectroscopy techniques rely on immobilizing capture molecules onto electrode surfaces and/or monitoring impedance characteristics using electrodes in contact with test chamber solutions. A disadvantage of these techniques is interfacial polarization, which occurs at the fluid-electrode interface. The restriction of charge transfer at the interface between electrically dissimilar materials (e.g. metal electrodes and buffer solutions) causes charge accumulation at the interface. The free charge carrier concentrations and associated carrier mobilities of the two (or more) dissimilar materials create a discontinuity in charge carrier concentration. The energy loss due to the relaxation of interfacial polarization has been classified as β-dispersion. Although changes in capacitance resulting from binding to capture molecules immobilized on electrode surfaces and β-dispersion can be used as a sensor transduction mechanism, interfacial polarization generally serves to interfere with the measurement of other forms of dielectric relaxation.

Another disadvantage of electrode contact with test chamber solutions is surface regeneration. The requirement for surface regeneration can occur over both short- and long-term time scales. In the short-term, non-specific binding of molecules in the test chamber, whether related to the analyte under investigation or simply present in the vehicle solutions, can irreversibly interfere with DRS measurements. Typically, electrode plates eventually foul, requiring system recalibration and/or regeneration. In some cases, electrodes must be recalibrated or regenerated before each measurement. Typical DRS measurement setups can also exhibit drift due to the harsh conditions required for surface regeneration. In the long term, the eventual loss of capture molecules or other surface structures that convey sensor specificity, or corrosion of the electrode material itself, often necessitate replacement of the sensor.

Dielectric relaxation spectroscopy can be used to measure properties of various materials, including liquids and gels. For example, DRS can be used to gain information about the size, structural characteristics, and electronic characteristics of an analyte. In some implementations, DRS can be used in sensor techniques, including being used as a biosensor.

Biosensors are broadly defined as devices which are capable of transducing biochemical events into measurable electrical or optical signals. The transducer is a feature of many biosensor designs, and many different transducing schemes have been proposed. FIG. 1 depicts a biosensor where biological detector molecules, such as antibodies or antigens, are immobilized onto a transducer surface.

A summary of the characteristics of two immunological techniques is presented in FIG. 2. Immunosensors typically possess similar sensitivity, specificity, and accuracy to well established immunologically based assays such as enzyme linked immunosorbent assays (ELISAs), with the added advantage of being rugged and providing the results in real-time and on-line. A specific example of a biosensor with immobilized immunospecies on its surface is the capacitance affinity sensor (CAS), described in U.S. Pat. No. 4,769,121.

The CAS utilizes the field produced by a parallel plate capacitor to measure changes to its biochemically active layer, where the detector molecules are located. The CAS, like most immunosensors, requires periodic surface regeneration. Surface regeneration has been recognized as a source of drift in these sensors's output signal, and can severely limit their longevity.

Typical biosensors developed to date rely on biological binding events occurring on or near the surface of an optical waveguide or an electrode. Biological molecules immobilized on surface materials must typically endure harsh chemical environments when the surfaces are regenerated between biosensing measurements, and in some cases the entire biologically activated surface must be replaced before every measurement.

One mechanism that has been used in biosensor applications is agglutination. One example of an agglutination-based immunosensor is the latex agglutination test (LAT), based on immuno-specific interactions. A common commercially available LAT that is sensitive, easy to use and inexpensive is the First Response® pregnancy test manufactured by Armkel LLC (Princeton, N.J.). LAT's typically require a fluid sample to be placed onto a surface (often white paper) which has been pre-loaded with antigen- or antibody-coated microspheres. Biological species in the fluid sample either cause or inhibit agglutination of biologically coated microspheres so that a visual, qualitative determination can be made about the presence of the biological species. However, results are largely qualitative and, as configured above, are generally designed for single-use applications.

SUMMARY

In certain aspects, the present disclosure provides a DRS apparatus and methods that use a remote electrode. The remote electrodes have reduced contact, or preferably no contact, with a sample for DRS assessment, measurement, or testing.

Preferably, the remote-electrode DRS apparatus or methods reduce or eliminate one or more effects of electrode contact with the sample. For example, using remote electrodes may reduce or eliminate interfacial polarization or charge accumulation at the electrode/sample material interface. In further examples, the remote electrodes reduce or eliminate surface degeneration or temporary contamination or alteration of the DRS electrodes. This may also mitigate or eliminate any need to recalibrate, regenerate, or replace DRS electrodes.

In one implementation, a remote electrode DRS apparatus includes parallel plate electrodes disposed adjacent opposing sides of a tube or cell containing a sample. The cell may have different configurations, such as, for example, with one open and one closed end providing a stop-flow configuration, or with a plurality of open ends providing a flow-through configuration. The cell may have various sizes and shapes.

In a particular example, the cell has a closed end and is constructed from borosilicate glass. The glass cell is secured in position by a Lucite cell holder. The side walls of the cell holder abut external opposing parallel plate electrodes.

In certain disclosed remote electrode DRS apparatus, the remote electrodes are sized and located so that the sample is located within the external boundaries of the electrodes and not exposed to stray fields, such as those that may occur between the plate electrodes near their edges. When a glass sample cell is used, insulation provided by the glass cell may reduce or eliminate DC conductivity between the electrodes and the sample.

In one example of a disclosed DRS technique, which can be used with a remote-electrode DRS apparatus, particles in a sample are used to determine the presence or concentration of an analyte in the sample. For example, the particles may be used to amplify or control DRS signals, such as by interacting with counter ions in the sample. Particles include microparticles and nanoparticles, such as microspheres or nanospheres. In certain embodiments, the particles are made from latex, glass, or polystyrene. In other examples, the particles are natural particles, such as blood cells or milk particles. The particles may be added to the sample or may be endogenous to the sample.

Different sized particles can be used for different purposes. The range of particle sizes that may be used may be influenced by signal-to-noise, environmental, and practical considerations (such as measurement sensitivity and particle settling time).

The particles may be charged or uncharged. In certain examples, the particles may include an insulator, conductor, or semiconductor. The size and electronic properties may be used to control or amplify DRS signals.

In one embodiment, a disclosed remote-electrode DRS technique uses particles having a diameter of about 0.01 to 10 µm in diameter, such as polystyrene microspheres. Such particles may have characteristic relaxation frequencies ("CRF", the frequency at which a maxima in a DRS response appears) of about 400 Hz to about 200 kHz. In particular examples, ionic polarization is the primary dielectric relaxation mechanism of samples containing such particles. Disclosed methods may be utilized to determine particle properties or assess an analyte, including real-time or on-line assessment.

In certain embodiments, a disclosed DRS apparatus and method, which may involve a remote-electrode DRS apparatus, use specially or functionally coated particles to enhance detection of the presence or concentration of one or more components of a sample. For example, specially coated particles may interact with an analyte in the sample to induce or alter the properties of counter ions in the sample, such as their distribution in the sample, or to alter the size or distribution of the particles. Resulting changes in DRS signal amplitude at distinct dielectric relaxation frequencies can provide an indication of the presence, and preferably the concentration, of the component. A fresh aliquot of particles may be added to the sample to provide a fresh active surface for interaction with the sample.

In certain embodiments, the disclosure provides a method for determining the concentration of a sample component. In one example, the particles agglutinate in the presence of analyte and the analyte concentration is determined at least substantially according to the formula:

$$[A]=K \cdot (R-R_{min})$$

where [A] is the analyte concentration, K is a constant, R is the ratio in the presence of a sample of the amplitude at a characteristic relaxation frequency of agglutinated particles to the amplitude at a characteristic relaxation frequency of unagglutinated particles; and $R_{min}$ is the ratio in the absence of analyte of the amplitude at a characteristic relaxation frequency of agglutinated particles to the amplitude at a characteristic relaxation frequency of unagglutinated particles. In further examples, the method includes measuring R, $R_{min}$, or K. For example, K may determine empirically.

According to the method, an amplitude A1 is measured at a characteristic relaxation frequency of agglutinate particles. An amplitude A2 is measured at a characteristic relaxation frequency of unagglutinated particles. A ratio R1 is calculated by dividing A1 by A2. R2 is determined by dividing A3 by A4, where A3 is the amplitude at the characteristic relaxation frequency of agglutinated particles in the absence of the analyte, and A4 is the amplitude at the characteristic relaxation frequency of unagglutinated particles in the absence of the analyte. A value R3 is determined by subtracting R2 from R1. R3 is multiplied by a constant term to give the concentration of the component. In certain embodiments, the contrast term is determined empirically by preparing standard curves.

The type of coated particles used in a given situation may be selected to detect or assess one or more analytes in a sample. Coatings for particles include analyte ligands, including ligands such as analyte proteins, agglutinating agents, and antibodies (such as polyclonal or monoclonal antibodies).

In certain examples, the DRS apparatus and method may measure agglutination of a coated particles and an analyte. Conversely, a DRS apparatus and method may initially utilize agglutinated particles to enhance the ability to detect one or more compositions or analytes that may un-agglutinate initially agglutinated particles. In either method, resulting changes in DRS signal amplitude at distinct dielectric relaxation frequencies can provide an indication of the presence, and preferably the concentration, of an analyte.

In another aspect, ionic polarization of a charge cloud surrounding particles may be used to sense particle distributions within a sample, including using a DRS apparatus that uses remote electrodes. For example, different sized particles may behave differently in different environments. Accordingly, disclosed DRS techniques may be used distinguish between, or separately assess, two or more analytes in a sample. In certain examples, such DRS techniques may be utilized to identify or dynamically track different particle populations.

There are additional features and advantages of the present invention or varying embodiments of the present invention. They will become as this specification proceeds.

In this regard, it is to be understood that this is a brief summary of varying aspects of the present invention or various embodiments or alternative embodiments of the present invention. The present invention therefore need not provide all features noted above nor solve all problems or address all issues in the prior art noted above.

DETAILED DESCRIPTION

Dielectric Relaxation Spectroscopy

Dielectric relaxation spectroscopy (DRS) measures the ability of a material to polarize itself within an electromagnetic field. DRS measurements are performed in the time domain by applying a step voltage and measuring the resultant transient flow of charge, or in the frequency domain by measuring the ability of the material to pass alternating current (AC) at different frequencies. Although this disclosure, including the Examples, utilize frequency domain DRS, the apparatus and principles disclosed herein may also be applied to time domain DRS.

Figure 3A:
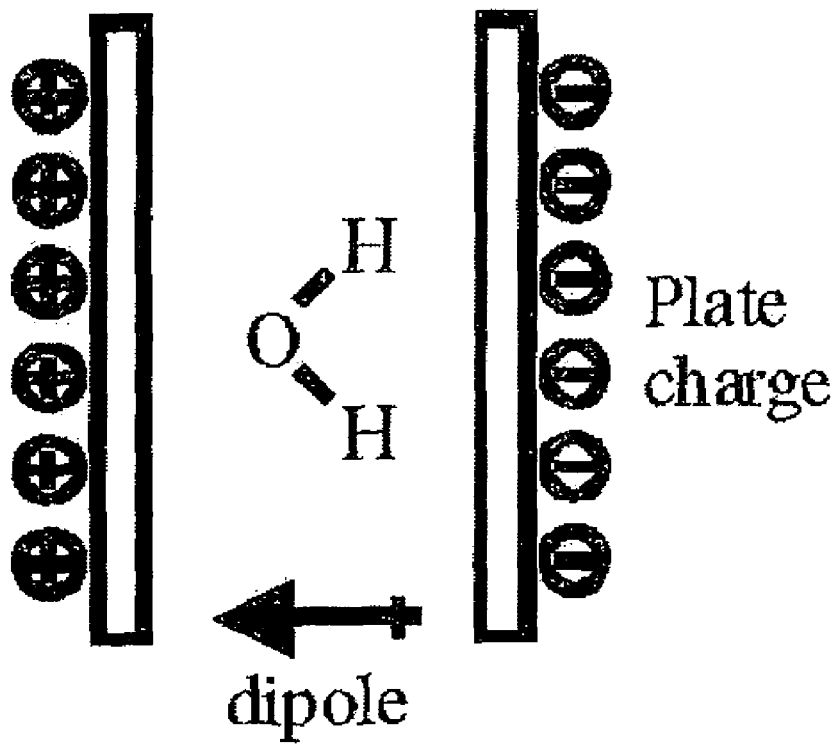
FIG. 3 is a schematic diagram of the dielectric relaxation spectroscopy technique.
Figure 3B:
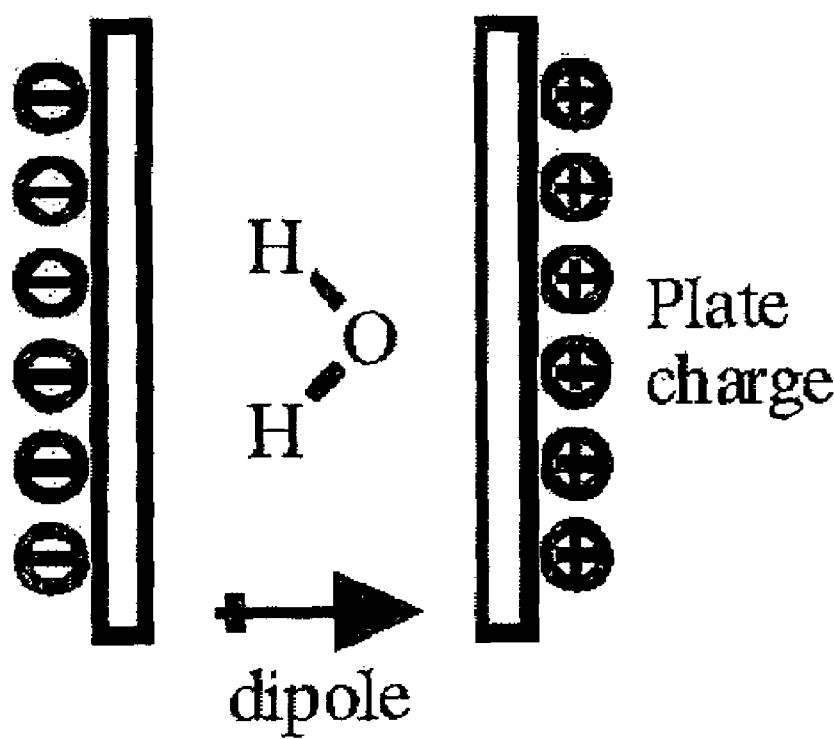

As shown in FIG. 3A, in frequency domain DRS, a time varying (AC) signal is placed across capacitor plates and substances with permanent dipoles orient themselves within the applied field to minimize their electrical potential energy. As shown in FIG. 3B, at sufficiently low frequencies, the substances instantaneously reorient as the polarity of the capacitor plates changes with the oscillating field. As the applied frequency increases, the substances reach a point where they can no longer keep up with the changing polarity of the field, and the reorientation process is no longer instantaneous. The dipoles eventually become 180° out of phase with the alternating electric field. The frequency where this occurs is commonly referred to as the characteristic relaxation frequency (CRF) of the substance. At frequencies above the CRF, the substances relax to a random orientation. Dielectric relaxation due to the polarization of permanent dipoles is also called γ-relaxation.

Figure 4A:
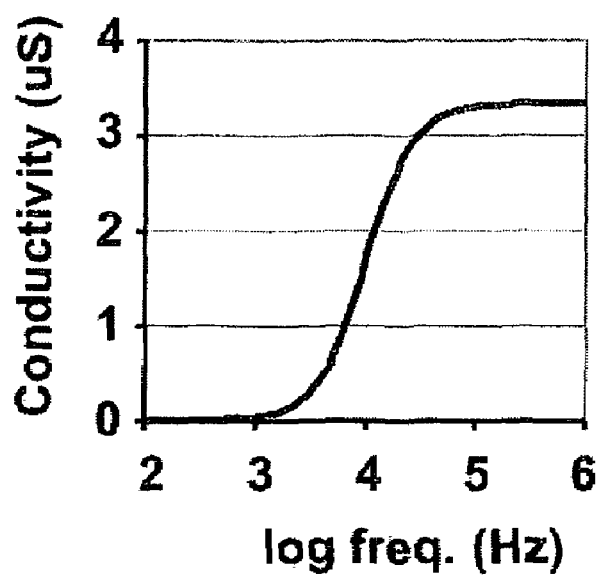
FIG. 4 is a graph of theoretical dielectric relaxation data for a material with a characteristic relaxation frequency of 10 Hz.
Figure 4B:
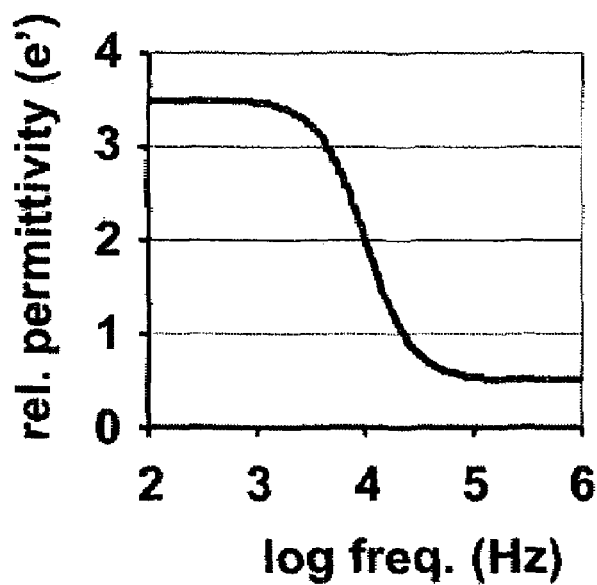
Figure 4C:
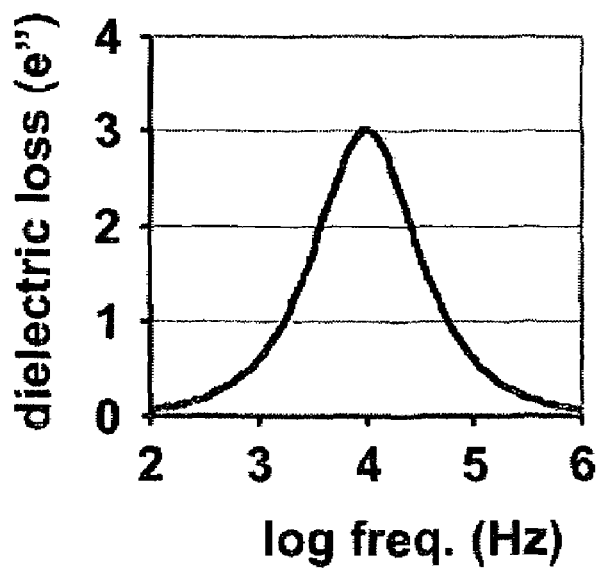

FIG. 4 depicts theoretical DRS data for a material whose CRF is 10 kHz. While the applied field oscillates near the relaxation frequency of the material, the energy going into the system is no longer stored in the form of electrical potential energy, but is dissipated as heat. As shown in FIG. 4A, this net absorption of energy increases the sample's conductivity. Simultaneously, as shown in FIG. 4B, the sample's relative permittivity is decreased because it is less able to store electrical potential energy. FIG. 4C illustrates that dielectric loss (∈") is maximum at the CRF. These dielectric phenomena can be used as a non-invasive means of characterizing molecular interactions.

The dielectric loss (∈") of material in the glass cell can be measured as a function of conductivity, according to:

$$\varepsilon'' = \frac{\sigma - \sigma_0}{\omega \varepsilon_v} \qquad \text{(eqn. 1)}$$

where $\sigma$ is the measured conductivity, $\sigma_0$ is the dc conductivity, $\omega$ is the angular frequency, and $\in_v$ is the permittivity of free space.

Figure 5A:
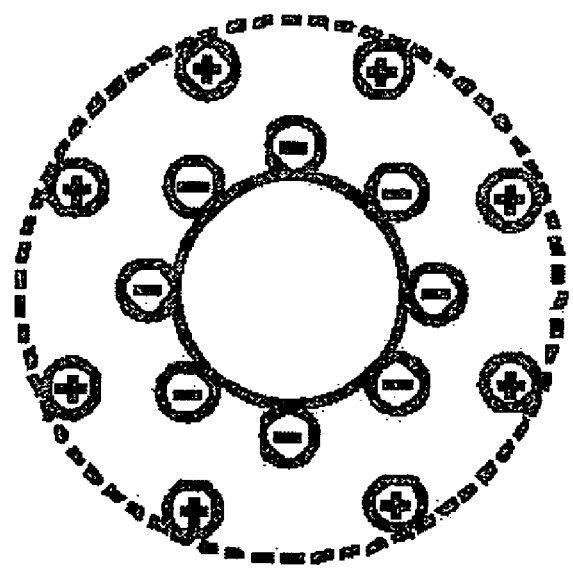
FIG. 5 is a schematic diagram of ionic reorientation of a counter ion cloud surrounding a particle when a field is applied.
Figure 5B:
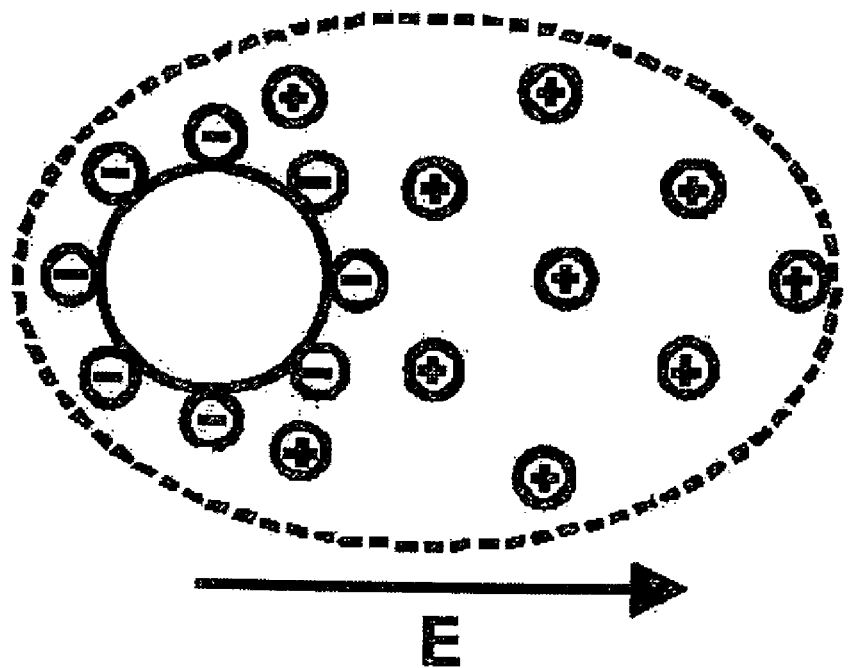

Substances lacking a permanent dipole may still exhibit dielectric relaxation. This is due to the formation of a counter ion cloud. For example, in the case of particles, such as polystyrene microspheres, in an electrolytic solution, the negative surface charges on the microsphere attract a cationic counter ion cloud. The negative surface charges on the microsphere and the associated cationic counter ions form an electrical double layer, described by the dashed line in FIG. 5A. In the presence of a time varying field, the bound negative charges on the microsphere will tend toward the anodic capacitor plate, while the positively charged counter ions will tend toward the cationic capacitor plate, as shown in FIG. 5B. Dielectric relaxation due to ionic species traveling over fixed path lengths is also called α-relaxation.

Interfacial polarization, a third type of dielectric relaxation, is due to charge accumulation at the interface between electrically dissimilar materials. Interfacial polarization, also called β-relaxation, is typically observed in cell suspensions due to the conductivity of the suspending fluid and the capacitive, insulating nature of the cellular membrane. Table 1 summarizes α, β, and γ dielectric relaxation, along with their associated polarization mechanisms.

TABLE 1

Summary of Relaxation Types
and Corresponding Polarization Mechanisms

| Relaxation Type | Polarization Mechanism |
| --- | --- |
| α-relaxation | Migration of surrounding species |
| β-relaxation | Charge accumulation at electrically dissimilar surfaces |
| γ-relaxation | Permanent dipole reorientation |

Figure 6:
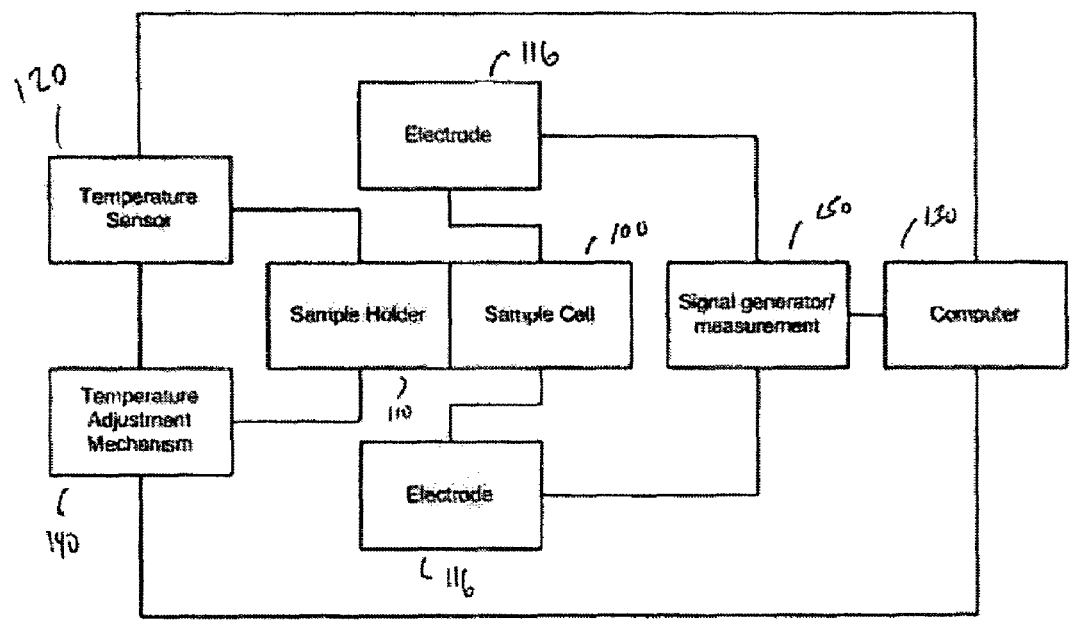
FIG. 6 is schematic diagram of components of a typical dielectric relaxation spectroscopy apparatus.

A schematic diagram of components of a typical DRS apparatus is shown in FIG. 6. A sample cell 100 for containing a sample is in communication with a sample holder 110. A pair of electrodes 116 are positioned proximate the sample holder. A temperature sensor 120 is optionally in communication with the sample cell 100 or sample holder 110 and a computer 130. The computer 130 may optionally be in communication with a temperature adjustment system 140, such as an air stream whose temperature is controllable, a liquid bath, or any other suitable temperature controlling means. An electronic signal generator and measurement device 150, such as an impedance/gain phase analyzer, is in communication with the electrodes 116 and the computer 130 through a suitable connection, such as an IEEE-488 connection. A suitable impedance/gain phase analyzer is model SI 1260A, available from Solartron Analytical of Farnborough, UK. A variety of software programs may be running on the computer 130, such as LabView (available from National Instruments of Austin, Tex.), Excel (available from Microsoft Corp. of Redmond, Wash.); and Origin Pro (OriginLab Corp., of Northampton, Mass.).

Figure 7:
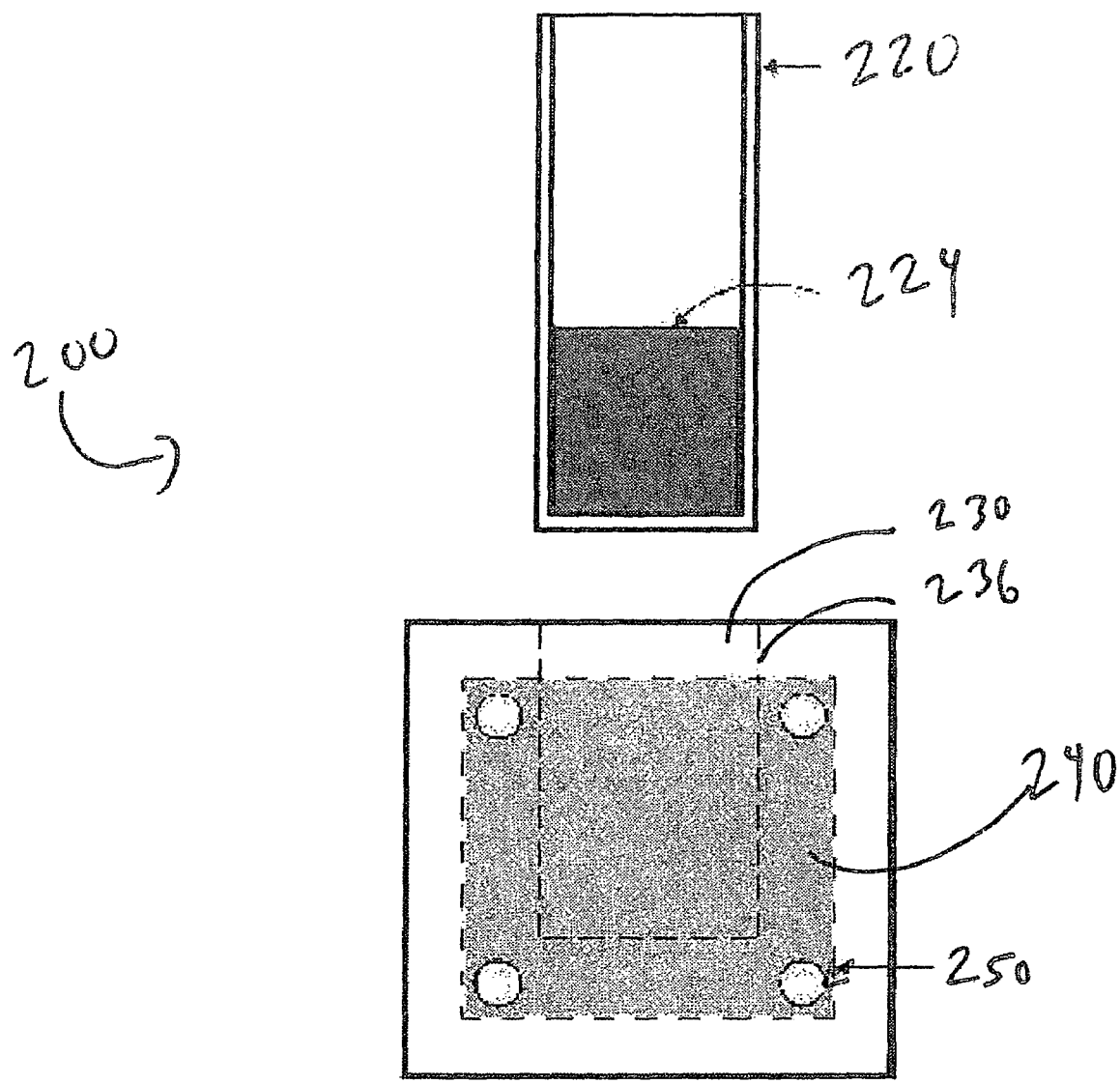
FIG. 7 is a schematic diagram of a dielectric relaxation spectroscopy apparatus according to an embodiment of the present disclosure.
Figure 8:
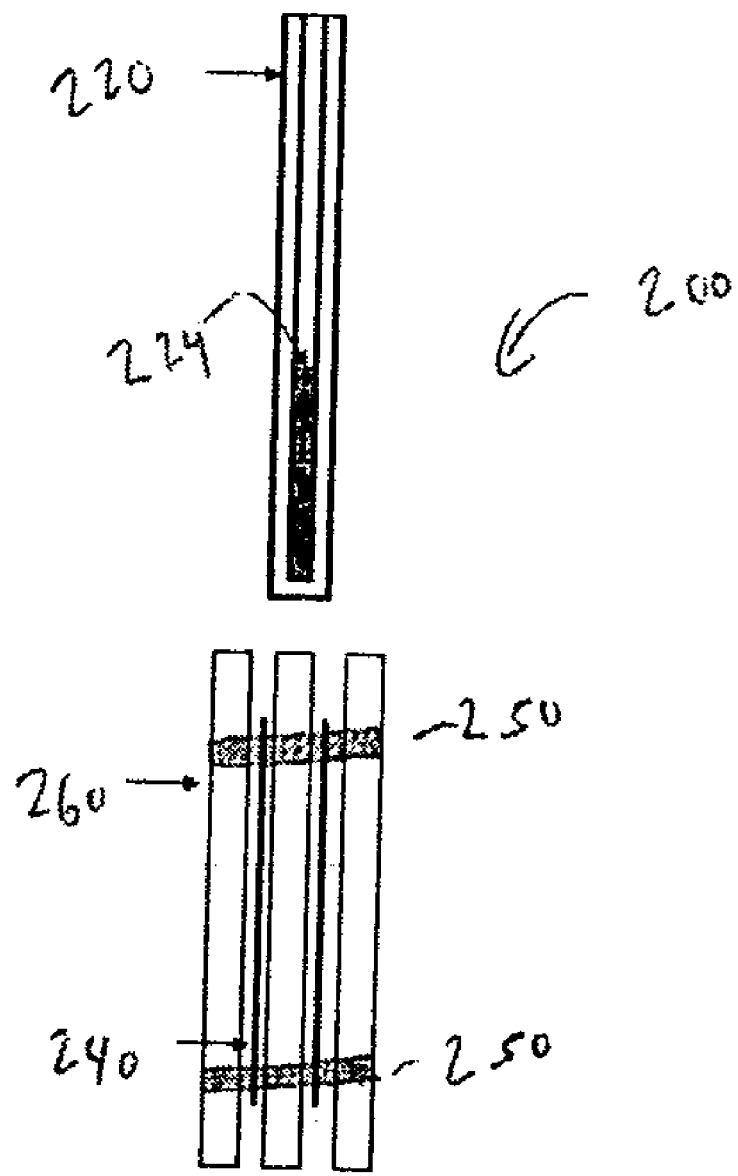
FIG. 8 is an alternate view of the dielectric relaxation spectroscopy apparatus of FIG. 7.

In certain embodiments, disclosed DRS apparatus utilize remote electrodes. An example of a remote electrode DRS apparatus 200 is shown in FIGS. 7 and 8. As shown in FIG. 7, a DRS apparatus 200 includes a sample cell 220 containing a sample 224. The sample cell 220 may be made of any suitable material that suitably transmits the radiation used in the DRS technique. For example, the sample cell 220 may be made from borosilicate glass, such as rectangular glass tubing, part no. CRT0220, available from Wale Apparatus of Hellertown, Pa. As shown in FIG. 7, the sample cell 220 has a closed bottom end and an open top end. This arrangement allows convenient washing and loading of the sample cell 220 while maintaining a stable physical environment during the measurement process. Of course, other sample cell 220 arrangements, including different sizes and shapes of sample cells 220, may be used. For some applications, it may be convenient to construct a sample cell 220 having a flow-through or stop-flow configuration where the volume within the plates is simply flushed between sample periods. The flow-through arrangement can increase the rapidity of sample and solution changes and may allow for on-line measurement. It is even possible to exchange, or dispose of and replace, sample cells 220 without significant alignment issues.

The DRS apparatus 200 includes a sample holder 230 and electrodes 240. The sample holder 230 may be constructed from materials that suitably transmit the radiation used in the DRS technique, such as Lucite or borosilicate glass. The sample holder 230 has a cut-out section 236 that is dimensioned to receive the sample cell 220. In at least certain examples, the cut-out section 236 is positioned such that the sample 224 will not be exposed to non-uniform stray electric fields occurring between the electrodes 240 near their edges.

The electrodes 240 may be any suitable size and shape and may be constructed from any suitable material. In one example, the electrodes 240 are brass plate electrodes. Preferably, the electrodes 240 are of sufficient size to encompass the sample cell 220 when the sample cell 220 is inserted into the cut-out section 236. Typically, the electrodes 240 and the cut-out section 236 are positioned and dimensioned such that the sample cell 220 will be positioned within the boundaries of the electrodes 240 when inserted into the cut-out section 236 of the sample holder 230. The electrodes 240 and sample holder 230 may be secured together, such as with fasteners 250, for example, nylon screws. The electrodes 240 may be connected to data acquisition, data analysis (such as an impedance analyzer), and current generating hardware (FIG. 6) through various types of connectors (not shown) and wires. In a particular example, the electrodes 240 are connected to external equipment using copper wire and BNC connectors. For example, two connectors may be used to apply voltage and two connectors may be used to measure current.

As shown in FIG. 8, supports 260 may be added on either side of the electrodes 240. The supports 260 may be constructed from the same types of materials as the sample holder 230, such as Lucite. The fasteners 250 may also be used to secure the supports 260 to the sample holder 230 or electrodes 240.

In contrast to typical DRS apparatus, in the DRS apparatus 200, fluid does not touch the electrodes 240. Accordingly, the disclosed DRS apparatus 200 allows information to be collected using only the electric field between the electrodes 240.

The disclosed DRS apparatus 200 may provide a number of advantages. For example, since fluid does not contact the electrodes 240, sample components, such as proteins and other substances, sticking to the electrodes 240 is not a concern. In addition, there is no need to compensate for dc conductivity ($\sigma_0$). DC conductivity can be a problem when analyzing DRS results because it can cause electrophoretic movement, which shows up as low frequency noise. Another advantage is the elimination of interfacial polarization effects, which occur in typical DRS setups. Interfacial polarization can be a problem at the electrode surface due to the electrode charge transfer resistance. Input capacitances can be very high and swamp the sample (measured) capacitance. The DRS apparatus 200 does not allow the conducting fluid medium to contact the electrode surface, and electrode polarization is therefore not a problem.

If desired, the temperature of the DRS apparatus 200, particularly of the sample cell 220, may be controlled during an experiment. Accordingly, the DRS apparatus 200 may be provided with a temperature sensor (FIG. 6). The temperature can be adjusted by any suitable means (FIG. 6), including a heated or cooled air stream or a temperature controlled liquid bath.

In certain embodiments, the sample holder 230 is configured to accommodate a considerably smaller sample cell 220. A smaller sample cell 220 allows smaller fluid sample volumes (e.g., about 100 µl) to be used. Such smaller sample cells 220 may be particularly useful in sensor applications using particles (discussed further below). For example sample volumes on the order of 100 µl could contain orders of magnitude fewer particles interacting with orders of magnitude fewer analyte molecules. Accordingly, sensitivity can be reported as number of measured species per 100 µl. For example, if $1 \times 10^9$ of an analyte species induced measurable agglutination of particles in a 100 µl sample volume, the DRS apparatus 200 would be detecting $1.66 \times 10^{-11}$ M analyte. In certain embodiments, the DRS apparatus detects analyte concentrations as low as $1.28 \times 10^{-10}$. The number of agglutinated complexes should normally be sufficient to provide measurable admittance and phase angle changes.

The DRS apparatus 200 may be constructed to generate a high capacitance (C) during alternating current (AC) measurements in order to maximize signal versus noise. For example, the dimensions of the electrodes 240 and sample cell 220 may be selected to maximize surface area (A) while minimizing the distance (d) between the electrodes 240, in accordance with general capacitance theory, $$C = \in_0 \in_v A/d \qquad \text{(eqn. 2)}$$

where $\in_0$ is a dielectric constant and $\in_v$ is the permittivity of free space ($8.854 \times 10^{-12}$ F/m).

Using an impedance analyzer set to measure admittance (Y) and phase angle ($\phi$), conductivity ($\sigma$) can be calculated as:

$$\sigma = |Y|\cos(\phi) \cdot \frac{d}{A} \qquad \text{(eqn. 3)}$$

As the frequency of the applied AC signal increases, the impedance of the parallel plate capacitor decreases, and the admittance increases correspondingly. At the CRF, the dielectric material in the test chamber is 180° out of phase with the applied AC field, and the phase angle reaches a local minimum due to the AC current passed through the capacitor.

Dielectric loss ($\in$") can be measured at uniformly distributed frequencies on a log scale from 100 Hz to 1 MHz. The equation for (unitless) dielectric loss is:

$$\varepsilon'' = \frac{\sigma - \sigma_0}{\omega \varepsilon_v} \qquad \text{(eqn. 4)}$$

where $\sigma$ is the frequency-dependent conductivity, $\sigma_0$ is DC conductivity, and $\omega$ is $2\pi$ multiplied by the applied frequency. Because, in the DRS configuration of FIGS. 7 and 8, there is glass insulation between the electrodes and the test fluid, there is essentially no DC conductivity and the $\sigma_0$ term can be ignored.

Particles

In certain embodiments, particles are added to substance to probed by DRS. The addition of particles may be particularly useful when sensing is performed remotely to maintain functional aspects of the environment under interrogation.

In certain examples, the particles are microparticles or nanoparticles (the terms "microparticles" or "nanoparticles" may be interchangeably used to refer to particles having a diameter of about 1 nm to about 999 µm, unless the context clearly indicates otherwise), such as microspheres or nanospheres. For example, the particles may have a diameter of about 5 nm to about 500 µm, such as about 10 nm to about 100 µm, such as about 10 nm to about 10 µm. The particles may be made from any suitable material, including glass or latex, polystyrene, or other synthetic materials. In further examples, the particles may be natural particles, such as blood cells or milk particles.

The size of a particle is correlated to its CRF. For example, particles with diameters of about 0.01 to about 10 µm typically exhibit CRF frequencies of approximately 400 Hz to 200 kHz. Accordingly, particles can be used to amplify and select the frequency range of DRS responses. Besides altering the DRS response, particles may provide other benefits. For example, if all activated surfaces reside on these particles, then the process of regenerating the sensing mechanisms consists simply of replacing the particles with a fresh aliquot. In many applications, because of the large size of the particles relative to the molecular species being sensed, it is also possible (if desired) to separate the particles from the sample for the purposes of containment or re-cycling. Any suitable separation method may be used, including filtration or sedimentation (such as centrifuging the sample and decanting the sample from the particles).

The range of useful particle sizes, and corresponding CRF frequencies appropriate for application as a sensing mechanism, may be selected using signal-to-noise, environmental, and practical considerations. The upper limit of particle size may determined both by measurement sensitivity and the settling time of the particles. In certain examples, dielectric relaxation due to particles with diameters greater than about 10 µm in an electrolytic solution results in small phase angle changes that become progressively more difficult to measure. This effect can be partially counteracted by increasing phase accuracy by increasing the number of measurements, although this may increase measurement times (particularly at lower frequencies). Larger particles also settle, due to gravity, more rapidly to the bottom of sample containment vessels, affecting their responses to applied AC fields compared to particles that remain suspended in solution. For example, typical 100 µm polystyrene microspheres settle at a rate of 0.27 mm/sec (TechNote 206, Bangs Labs). After 3 minutes (the time to conduct a typical DRS experiment) approximately 25% of 100 μm particles in a test solution will have settled to the bottom of a chamber with dimensions as described in Example 1. Settling can be partially counteracted by continuously vibrating the test chamber and its contents or through mechanical or magnetic stirring of the sample.

Manufacturability is another factor in determining the useful range of particle sizes. One commercial vendor (Bangs Labs, Fishers, Ind.) produces particles with diameters ranging from 0.01 μm to 999 μm.

As discussed further in Example 1, counter ions, including counter ions in a cloud surrounding a particle, typically relax by an ionic polarization (α-dispersion) mechanism. Because of the ionic polarization mechanism of the counter ion cloud, DRS methods employing particles typically exhibit dependencies on particle size, pH, and electrolyte concentration. However, the DRS results are typically insensitive to temperature variations in the limited range around room temperature. FIG. 9 is a conceptual illustration showing the principal methods for altering the dielectric responses of a typical DRS-particle system.

Figure 9A:
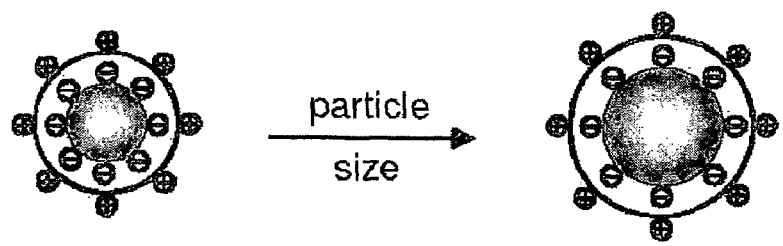
FIG. 9 is schematic diagram of the effects of particle size, electrolyte concentration, and ionic species on relaxation.
Figure 9B:
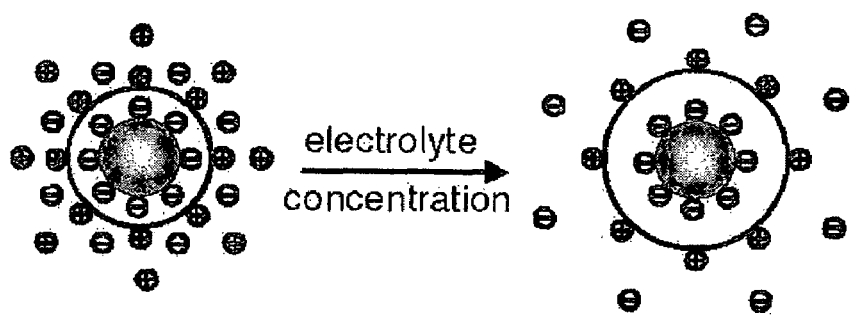

Without being limited by theory, as shown in FIG. 9A, increasing the diameter of particles increases the path length that the counter ions travel in response to changing polarity of the applied electric field. This results in a lower CRF with increasing particle size. If the influence of the particle on CRF is reduced, an inverse proportional relationship between particle size (such as the radius of spherical particles) and CRF may be observed.

Figure 1:
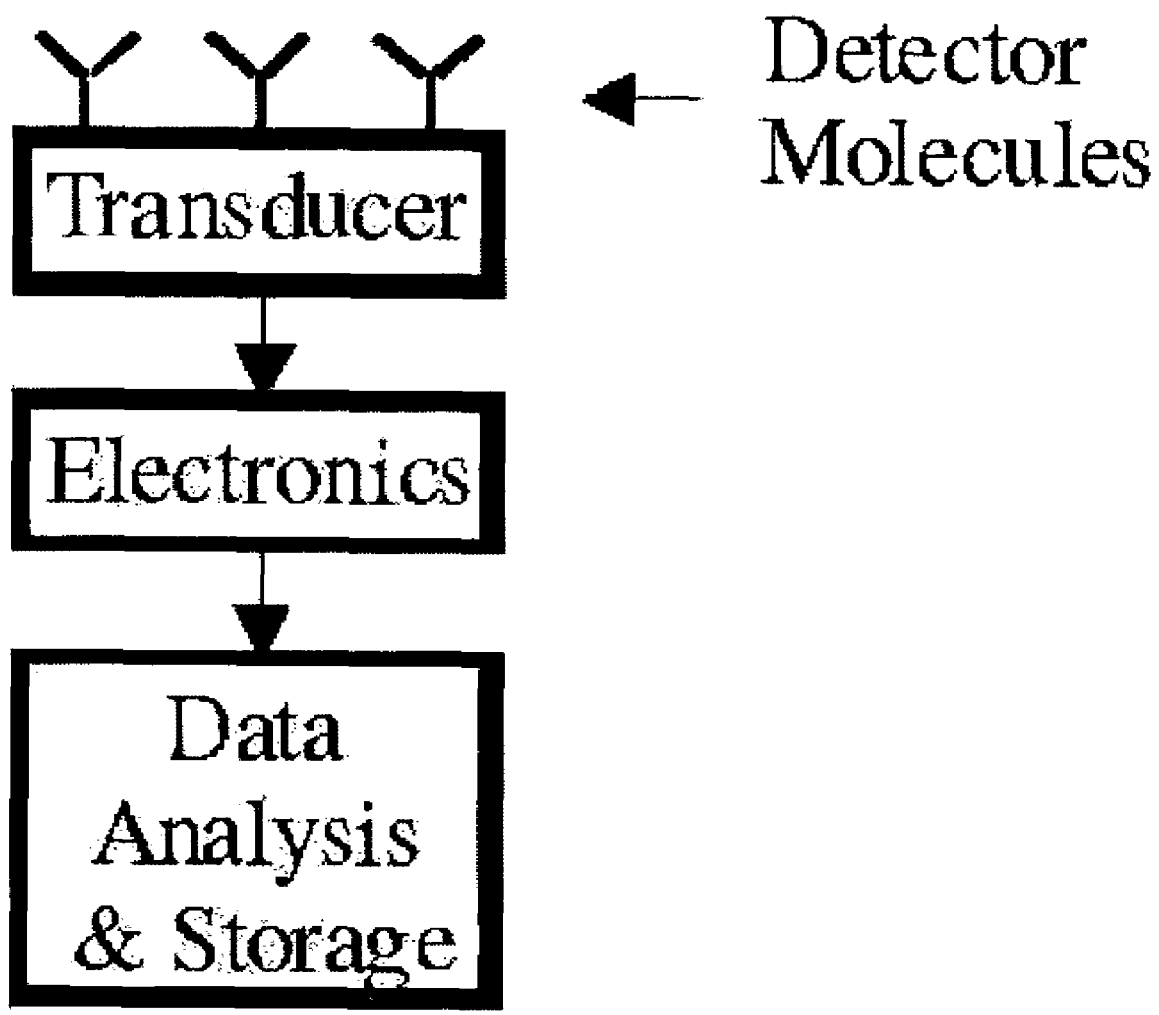
FIG. 1 is a schematic diagram of a biosensor.
Figure 2:
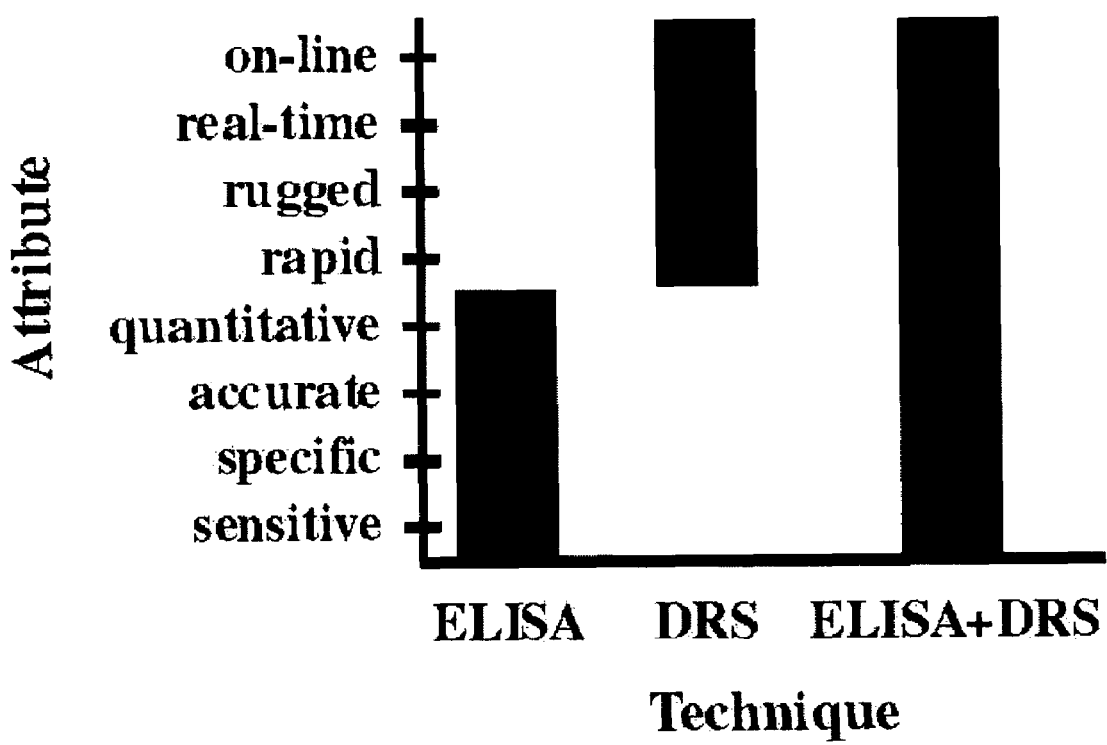
FIG. 2 is chart summarizing the attributes of various sensing techniques.

The electrolyte concentration of a sample may also affect the DRS response of a sample. Without being bound by theory, increasing the electrolytic concentration of the test sample solution is believed to shorten counter ionic path lengths by shrinking the size of the charge double layer (see FIG. 2.9B). Inter-ionic distance, d, has been estimated using this equation:

$$d = 0.95 \cdot c^{-1/3} \text{ nm} \qquad \text{(eqn. 5)}$$

where c is electrolyte concentration expressed in moles per liter. If inter-ionic distance is roughly inversely proportional to CRF, this would imply that CRF should be proportional to the cube root of concentration.

Figure 9C:
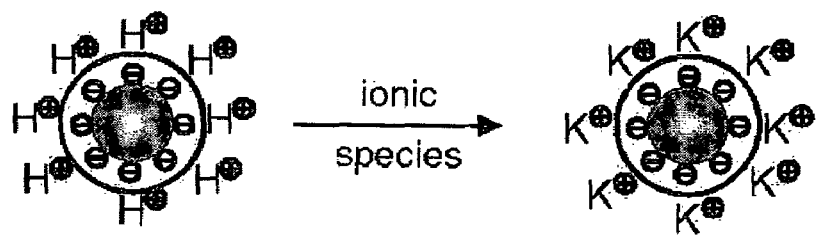
Figure 9D:
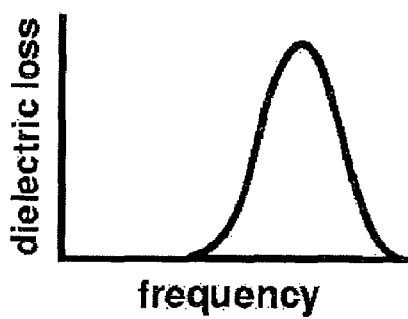
Figure 9E:
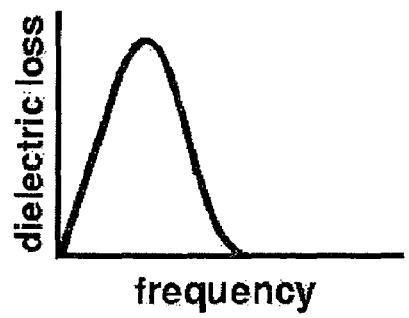

Another factor that can affect DRS results is pH. Test samples exhibiting α-dispersions should be sensitive to changes in pH, since pH can influence the nature of the counter ions. Without being limited by theory, for example, as illustrated in FIG. 9C, in a KCl sample, at low pH, counter ions are primarily $H^+$ because the surface chemistries on the particles are in their protonated form. As pH is increased, $K^+$ ions replace the $H^+$ ions within the counter ion cloud surrounding the particles. Theoretically this should cause the CRF to increase due to the inferior ionic mobility of $K^+$ ions compared to $H^+$ ions ($36.3 \times 10^{-8}$ $m^2/Vs$ for $H^+$ versus $7.6 \times 10^{-8}$ $m^2/Vs$ for $K^+$).

Sensor Applications

The number and size of particle complexes may vary based on the presence or absence of specific analytes. Because the DRS response of a sample depends upon the size of the analyte, or the size of analyte formations, changes in DRS response can be used to detect the presence or concentration of an analyte species. For example, by appropriate selection of the surface chemistries of the particles in a sample, agglutination (including un-agglutination) can be used as a mechanism to alter the size-distribution of particle complexes. This alteration of the size distribution produces a change in the DRS response of the sample.

A wide range of substances may be used to promote binding between a particle and an analyte of interest. For example, analyte binding substances or analyte. interaction substances may be included on the surface of the particles to bind or interact with an analyte. Exemplary coatings for particles include analyte ligands, including ligands such as analyte proteins, agglutinating agents, and antibodies (such as polyclonal or monoclonal antibodies). The term "ligand" as used herein refers to a molecule, or a domain of a molecule, which is able to bind or associate, including by covalent or non-covalent bonds, selectively to one or more specific sites on another molecule. Non-limiting examples of ligands include an antibody and its antigen, a hormone and its receptor, and an enzyme and its substrate. Using appropriately coated particles, DRS methods may provide useful sensors, such as biosensors, possessing useful properties, such as specificity, sensitivity, and response time.

DRS apparatus using remote electrodes can be used to make non-invasive measurements based on changes in sample properties, such as particle size and distribution, such as by agglutination. For example, the degree of agglutination can be tracked quantitatively in real-time as both a decrease in a higher frequency dielectric relaxation associated with singlet particles and an increase in lower frequency relaxation associated with multi-particle clusters. Ionic polarization in the vicinity of particle clusters (i.e. α-dispersion) typically remains the primary dielectric relaxation mechanism.

Because DRS is able to probe decreases in particle or particle cluster size, DRS sensors can also be setup to measure un-agglutination rather than agglutination. For example, un-agglutination can use a competitive assay using pre-agglutinated particles added to a sample. Analyte added to the sample competes with analyte already bound within pre-agglutinated particle complexes, resulting in fewer agglutinated complexes and more singlet particles. When analyzing the DRS data from a competitive assay, presence of the analyte of interest causes a decrease in amplitude of the lower frequency dielectric loss peak and a corresponding increase in the dielectric loss peak representing singlet particles. The assay can be designed with either the coating (such as an antibody) or the analyte immobilized onto the particle surface.

Utilizing particle coatings with different affinities allows tuning of DRS sensors. For example, an antibody-antigen model typically has a lower affinity than the streptavidin-biotin model described in Example 2. The higher on-off rate of agglutination interactions with lower affinities typically favors smaller cluster sizes, and vice versa.

Because of the interaction between the particles and the analyte, the resulting distribution of particles can be repeatedly interrogated by DRS techniques. The ability to repeatedly interrogate a sample serves as an amplification mechanism to detect the presence or absence of small numbers of analyte molecules.

The concentration of analyte or particles is preferably chosen to maintain a desired size of particle clusters. For example, high concentrations of analyte may cause the formation of small numbers of large clusters composed of large numbers of particles. Because DRS measurements typically depend on the total number of clusters of any size in solution, the largest clusters produce small DRS signals at extremely low frequencies. In addition, some clusters might become so large that they settle out of solution due to gravity.

The basic DRS sensor platform can be constructed in a number of different configurations for different applications. Parameters such as sample chamber size, the use of particles with different chemistries, sampling time required to acquire signals, fluid handling, power consumption, and electrode type, location, and configuration (including the choice to use remote or direct contact electrodes) can be adapted for different applications. For example, although it may be beneficial to use remote electrodes to avoid electrode contact with the sample, direct contact electrodes may provide higher signal-to-noise ratios in certain applications.

Applications of the apparatus and methods disclosed herein include invasive or non-invasive medical applications (such as detection through a subject's skin, for example). For example, the presence, absence, or degree of agglutination of blood cells can be measured.

Further applications include environmental measurements, such as detection of analytes within pipes or vessels containing fluids of interest, such as ground water. In certain implementations, the apparatus and methods disclosed herein may allow on-line, real-time measurements with results being rapidly available for interpretation and use in decision-making processes. Other applications include terrestrial, atmospheric, and aquatic analyte testing. For example, the presence or absence of particles can be used in quality control procedures, such as in checking the purity of milk.

The ability of the disclosed DRS apparatus, including when used as a sensor, such as a biosensor, to respond to new toxic chemicals, explosives, and biological agents can also be utilized in national security, industrial, healthcare, environmental, and military applications.

EXAMPLE 1

Polystyrene nanospheres are used to amplify and control the frequency range of DRS signals. In this configuration, the dominant dielectric relaxation mechanism is ionic polarization (α-dispersion).

Experimental

DRS Configuration

A sample cell was constructed according to the design shown in FIGS. 7 and 8. Borosilicate glass rectangular "tubing" used to hold fluid samples during DRS measurements was obtained from Wale Apparatus (part no. CRT0220; Hellertown, Pa.). The inner dimensions of the glass sample cell were 2×20×48 mm, with a 2 mm wall thickness. Accordingly, the outer width of the glass sample cell was 6 mm.

AC electric fields were generated by brass electrode plates (35.0×31.74×0.025 mm). The glass sample cell was held between the capacitor plates by a piece of Lucite with a U-shaped cutout. Two additional pieces of Lucite held by nylon thumb screws provide support from either side. The Lucite plates were 48 mm high and 43 mm long. The test fixture was connected to an impedance analyzer with copper wiring via four panel-mount BNC connectors (two to apply voltage and two to measure current).

Test sample temperature was maintained by a temperature-controlled air stream, similar to the setup utilized by Minor et al., J. Colloid Interface Sci., 206: 397-406, 1998. Sample temperature was measured with a thermistor temperature probe (YSI Temperature, Dayton, Ohio) attached to the outer surface of the glass sample cell. The temperature of the assembly was stable for at least one minute before a temperature-dependent measurement was recorded to ensure that thermal equilibrium had been achieved.

Materials

Polystyrene nanospheres were obtained from Bangs Labs (Fishers, Ind. USA). According to manufacturer's specifications, the density of the solid polymer for all nanospheres ranged between 1.05 and 1.06 g/cm$^3$. Nanospheres were shipped as 10% solids (volume %) in deionized water. Prior to performing DRS measurements, nanospheres were diluted in 600 μl of KCl solution where concentrations are indicated in each protocol below.

Buffers were created using reagent-grade components obtained from Sigma-Aldrich. All sample solutions were made with 0.2-μm filtered, deionized water. Buffer pH was adjusted using reagent-grade sodium hydroxide and hydrochloric acid.

Instruments and Hardware

DRS experiments were performed using an impedance/gain-phase analyzer (model SI 1260; Solartron Analytical, Famborough, England) placed within a grounded Faraday cage. The impedance analyzer was controlled via an IEEE-488 interface using LabView software (National Instruments, Austin, Tex.). Custom software developed in LabView was also used to acquire data and compute DRS responses. Other data analyses and display were performed using Excel (Microsoft) and Origin Pro (Microcal, Mass.). In all experiments, the impedance/gain-phase analyzer was set to an integration time of 1 second with five measurements per decade.

The maximum potential applied by the impedance spectrometer was 3 volts. With a spacing of 6 mm between electrode plates, this corresponds to a maximum field strength of approximately 5 V/cm. Even accounting for the non-uniform distribution of materials between the plates (with a high dielectric solution in the central 2 mm), this field is well below field strengths of 850 V/cm, or 500 V/cm reported to produce nonlinear dielectric effects.

Measurement Procedure

The impedance analyzer was set to measure admittance (Y) and phase angle (φ) from which conductivity (σ) can be calculated as:

$$\sigma = |Y|\cos(\phi) \cdot \frac{d}{A} \qquad \text{(eqn. 3)}$$

Figure 10A:
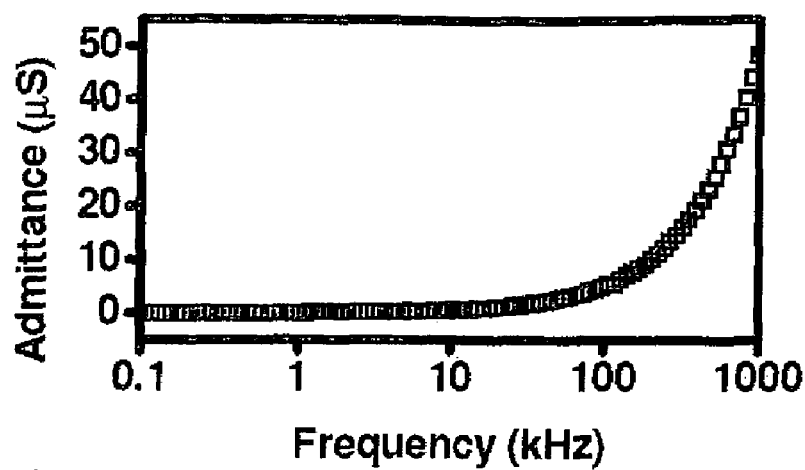
FIG. 10 is graphs of admittance and phase angle as a function of frequency.
Figure 10B:
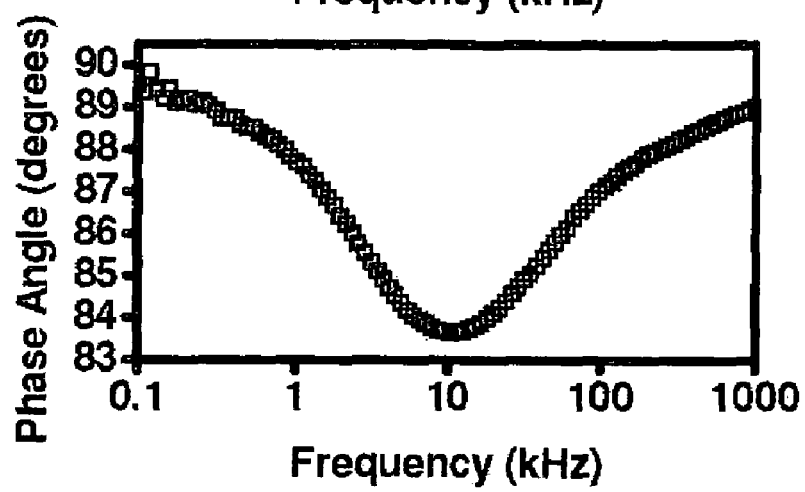

As the frequency of the applied AC signal increases, the impedance of the parallel plate capacitor decreases, and a corresponding increase in admittance is observed (FIG. 10A). At the CRF, the dielectric material in the test chamber is 180° out of phase with the applied AC field, and the phase angle reaches a local minimum due to the AC current passed through the capacitor (FIG. 10B).

Since the relative permittivity of water is 80 compared to 5 for borosilicate glass, the majority of the dielectric effect between the plates is contributed by the solution within the sample chamber volume. The minor contributions of any frequency-dependent series capacitance contributed by the side walls of the chamber and parallel capacitance around the chamber are components of the background that were subtracted from each trace, as described below. Thus, the geometry of the solution volume as shown in FIGS. 7 and 8 (having d=2 mm and the length of a side=24 mm minus 2 mm wall thickness from each end) results in a d/A term of 5.0/m.

Dielectric loss (∈") was measured at uniformly distributed frequencies on a log scale from 100 Hz to 1 MHz. The equation for (unitless) dielectric loss is:

$$\varepsilon'' = \frac{\sigma - \sigma_0}{\overline{\omega}\varepsilon_v} \qquad \text{(eqn. 4)}$$

where $\sigma$ is the frequency-dependent conductivity, $\sigma_0$ is DC conductivity, and $\omega$ is $2\pi$ multiplied by the applied frequency. Because there is glass insulation between the electrodes and the test fluid, there is essentially no DC conductivity and this term ($\sigma_0$) can be ignored.

Results

General DRS Response

Figure 11A:
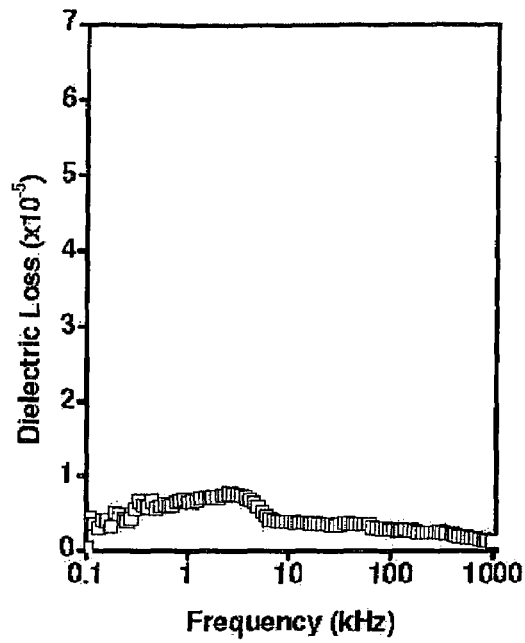
FIG. 11 is graphs of dielectric loss as a function of frequency for solutions of: (A) 600 µl 1 mM KCl (pH 5.0); (B) 600 µl of 1 mM KCl solution with 5 µl (10% solids) of 0.3 µm diameter nanospheres; and (C) dielectric relaxation response of the nanospheres minus the background response of the solution absent the spheres (i.e.
FIG. 11B minus FIG. 11A).

A sweep of bulk test solution was performed before adding nanospheres in order to characterize the frequency response of the test fixture and any dielectric properties of vehicle solutions. These data were treated as background and subtracted from sweeps collected after nanospheres were added to bulk solutions. FIG. 11A shows an example of a background sweep performed with 600 µl of 1 mM KCl solution in the glass measurement cell. The small, low-frequency dispersion around 4 kHz was observed in all bulk solutions measured and likely includes non-specific stray capacitance effects between components of the test fixture and electrodes.

Figure 11B:
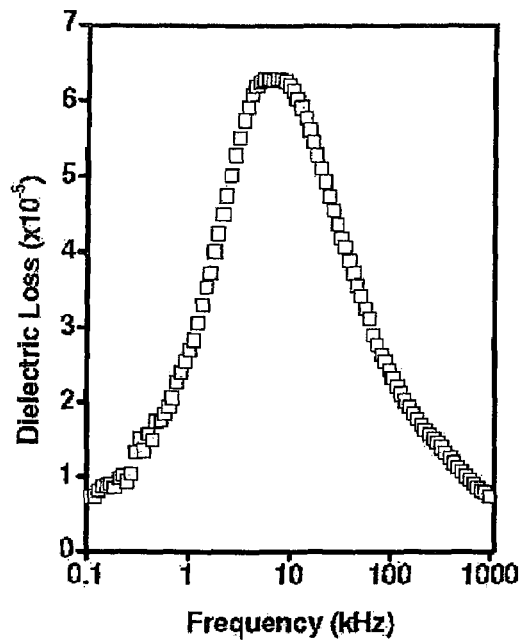
Figure 11C:
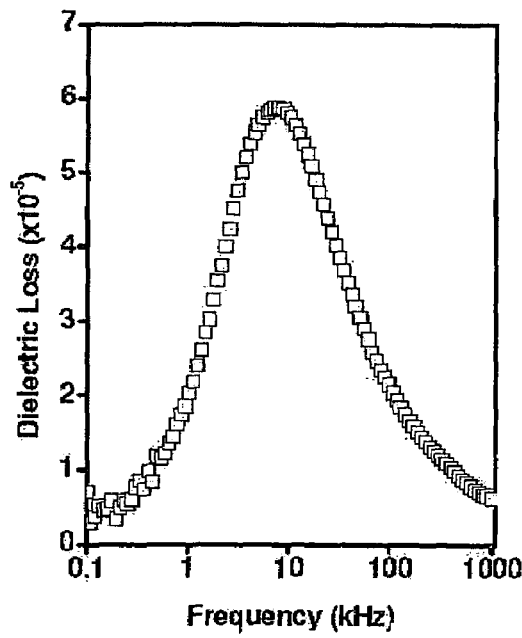

FIG. 11B shows raw data from a test sample consisting of the same bulk solution as in FIG. 11A with 5 µl (10% solid) of 0.3 µm diameter nanospheres added. The broadness of the peak in FIG. 11B suggests a non-Debye type relaxation, where two or more relaxation phenomena occur at frequencies near one another. FIG. 11C shows a typical dielectric loss trace, created by subtracting the background trace shown in FIG. 11A from the data trace shown in FIG. 11B. The narrower peak suggests that a single relaxation mechanism is dominant in the resultant dielectric response. The CRF at 8.7 kHz in samples containing polystyrene nanospheres is consistent with a counter ionic polarization or a-dispersion mechanism.

Effects of Particle Size

Figure 12A:
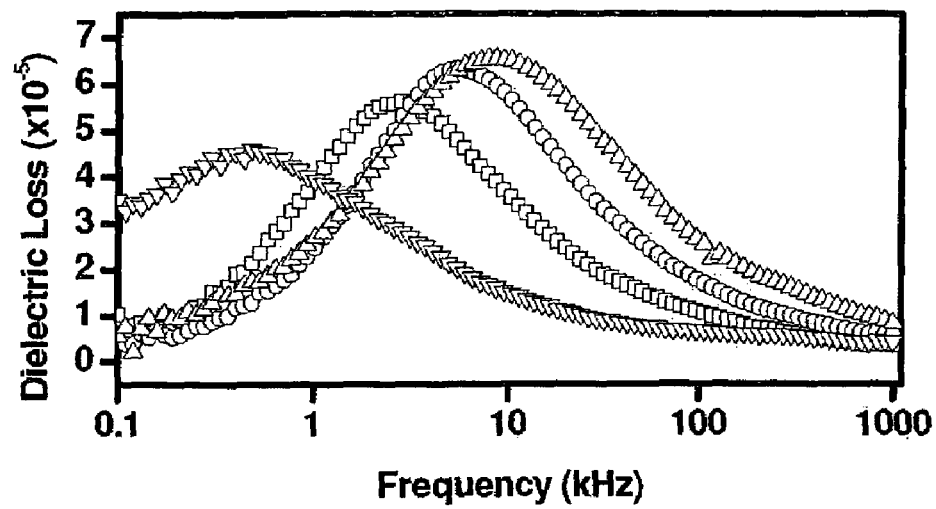
FIG. 12 is graphs of: (A) dielectric loss as a function of frequency for 5 µl of 10% solids nanospheres with diameters of 9.9 µm (inverted triangles), 1.0 µm (squares), 0.5 µm (circles), and 0.3 µm (triangles) in 600 µl of 1 mM KCl solution at pH 5.0; and (B) a least squares curve-fit to an equation of the form $a \cdot r^b$ of FIG. 12A.
Figure 12B:
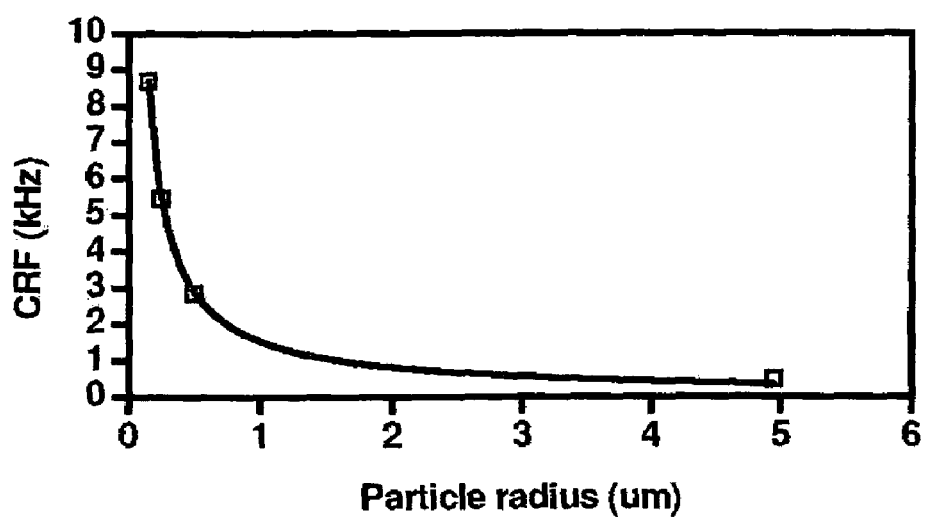

As discussed above, and without being bound by theory, during α-dispersion, the diameter of the nanospheres is believed to determine the path length over which counter ions travel in response to an applied field (FIG. 9A). Counter ions around larger particles have longer path lengths to follow when responding to an applied AC field. In order to investigate this effect, DRS responses were measured using nanospheres with diameters ranging from 0.3 to 9.9 µm in 600 µl of 1 mM KCl solution (FIG. 12A). CRFs were 9.9 µm: 0.5 kHz, 1.0 µm: 2.8 kHz, 0.5 µm: 5.5 kHz, and 0.3 µm: 8.7 kHz. CRFs were curve-fit (FIG. 12B) to an equation of the form $a \cdot r^b$ where least squares values of 1.1 kHz and −1.05 were determined for parameters a and b, respectively. CRF is inversely proportional to particle diameter with a proportionality constant of 1.5 kHz/micron.

Effects of Electrolyte Concentration

Figure 13A:
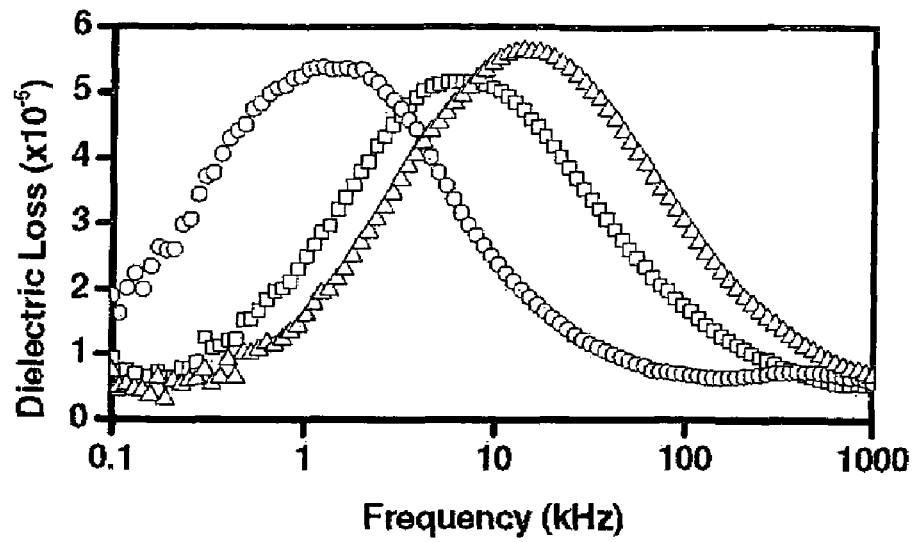
FIG. 13 is graphs of: (A) dielectric loss as a function of frequency for 5 µl (10% solids) of 0.50 µm diameter nanospheres in 600 µl of 0.1 mM (circles), 1.0 mM (squares), and 10.0 mM (triangles) KCl solutions; and (B) a least squares curve-fit of FIG. 13A to an equation of the form $a \cdot [c]^b$ CRF.
Figure 13B:
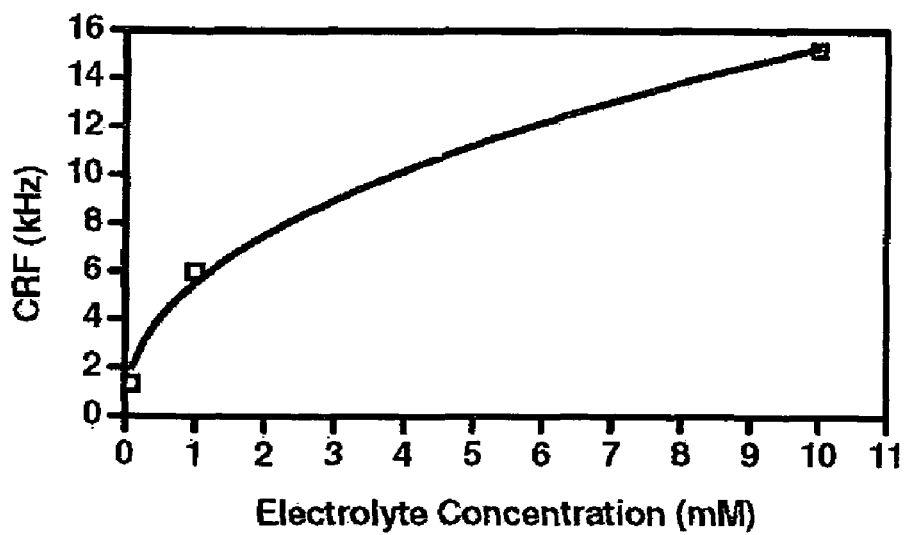

FIG. 13A shows DRS responses from 5 µl of 0.3 µm diameter nanospheres in 600 µl solutions containing 0.1 mM, 1 mM, and 10 mM KCl. For each solution, pH was set to 5.0. At different electrolyte concentrations, CRFs were 0.1 mM: 1.4 kHz, 1.0 mM: 6.0 kHz, and 10.0 mM: 15.2 kHz. The CRF increases with increasing electrolyte concentration (FIG. 13B) with an approximate 10-fold increase in CRF when the electrolyte concentration was increased 100-fold from 0.1 mM to 10 mM. When CRF data are curve-fit to an equation of the form $a \cdot [K^+]^b$, the optimum least-squares fit results in a power term, b, of 0.44 and a proportionality constant, a, of 5.5 kHz/mM.

Effects of pH

Figure 14A:
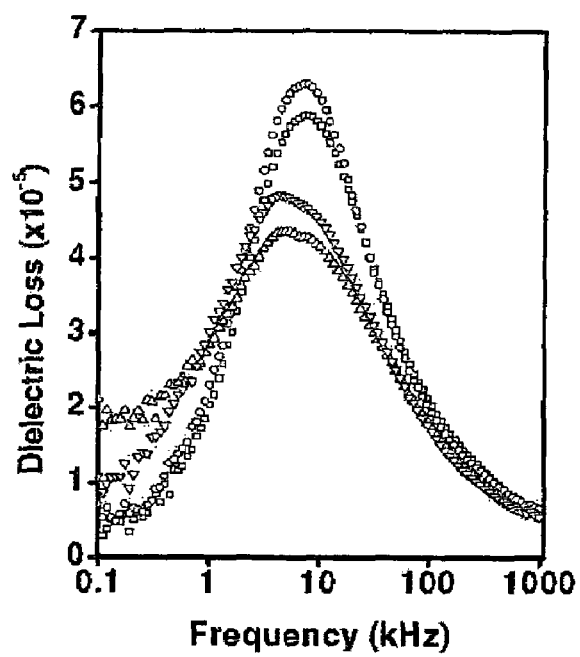
FIG. 14 is graphs of: (A) dielectric loss as a function of frequency for 5 µl (10% solids) of 0.30 µm diameter nanospheres in 600 µl of 10 mM KCl at pH 4.0 (circles), 5.0 (squares), 6.0 (inverted triangles), and 7.0 (triangles); (B) dielectric loss as a function of frequency for 5 µl (10% solids) of 0.30 µm diameter nanospheres in 600 µl of 10 mM KCl at pH 7.4 (squares), 8.0 (inverted triangles), 9.0 (triangles), and 10.0 (circles); (C) resultant CRFs from FIGS. 14A and 14B as a function of pH.
Figure 14B:
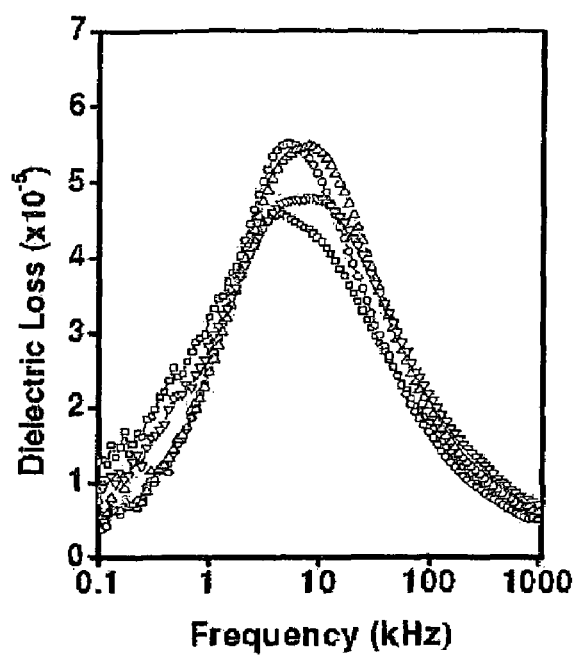
Figure 14C:
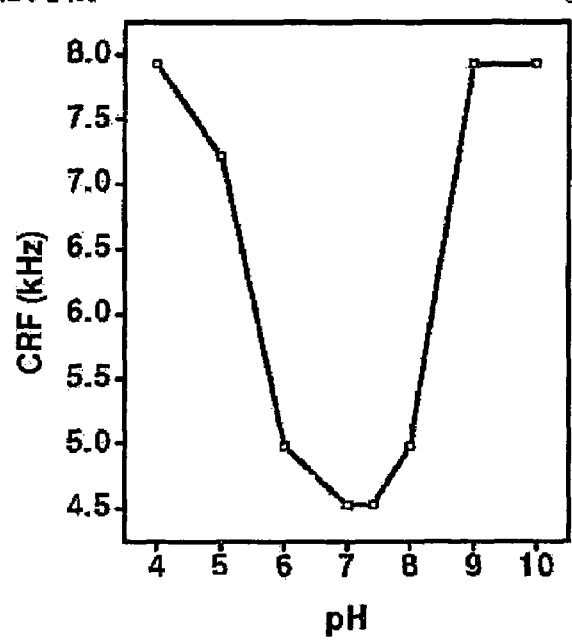

Nanospheres were suspended in solutions where pH was varied from 4.0 to 10.0. FIG. 14A shows dielectric loss curves for 0.3 µm diameter nanospheres in 10 mM KCl solutions with pH values ranging from 4.0 to 7.0. FIG. 14B shows dielectric loss curves for pH values from 7.4 to 10.0. At different pH values, CRFs were 4.0: 7.0 kHz, 5.0: 7.2 kHz, 6.0: 5.0 kHz, 7.0: 4.5 kHz, 7.4: 4.5 kHz, 8.0: 5.0 kHz, 9.0: 7.9 kHz, and 10.0: 7.9 kHz. FIG. 14C shows how CRF decreases as pH is varied from 4.0 to 7.0, and then increases as the pH is adjusted from approximately 7.4 to 10.0. Without being bound by theory, changing pH is believed to alter the ionic species and mobility of the counter ions surrounding the particles. At low pH, the counter ions are mostly $H^+$ ions. At pH values between 4 and 8, the counter ions are mostly $K^+$ ions (FIG. 9C). The increased ionic strength at pH's above 8 is believed to compress the electrical double layer where higher CRFs are observed.

Effects of Temperature

Figure 15:
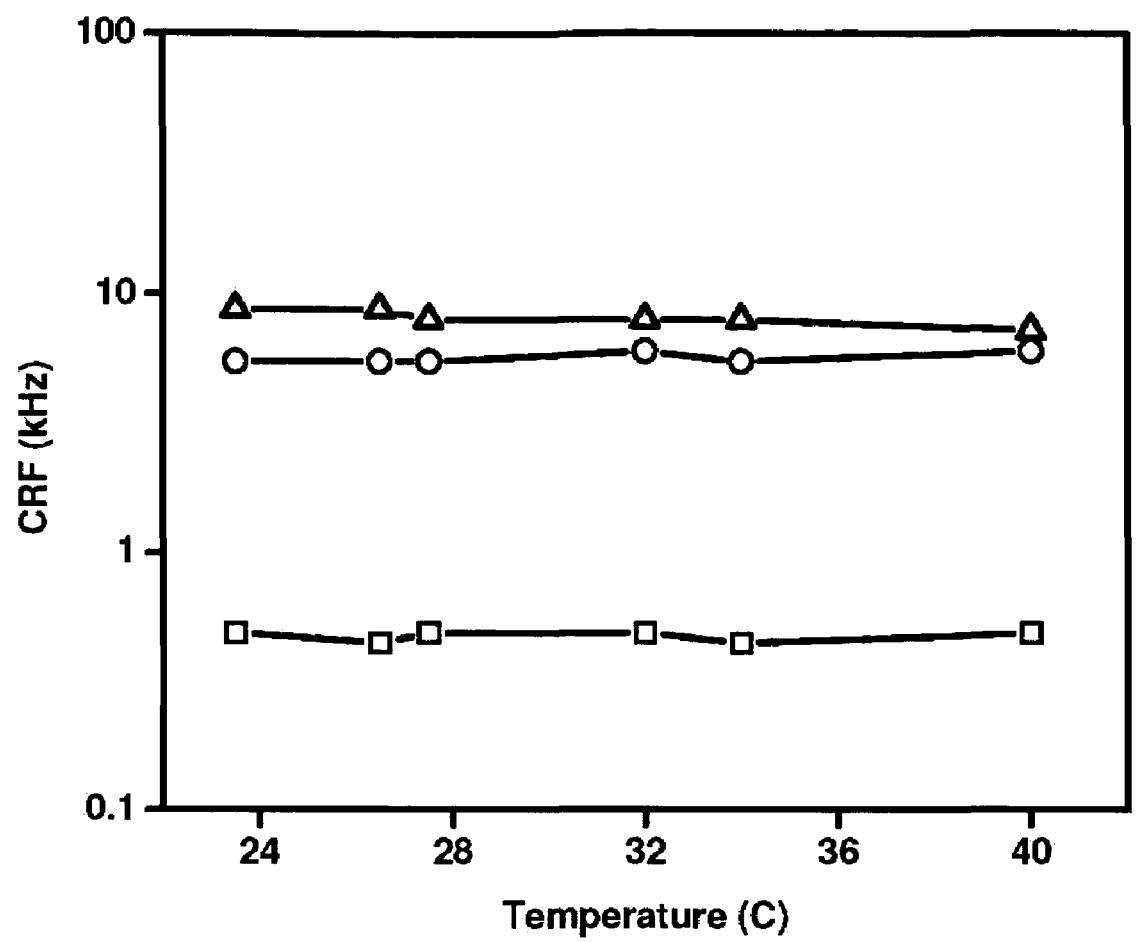
FIG. 15 is a graph of CRFs as a function of temperature from 23.5° C. to 40° C. for three samples, containing counter ions having diameters of 0.30 µm (triangles), 0.50 µm (circles), and 9.9 µm (squares) in 600 µl of 10 mM KCl.

FIG. 15 shows DRS measurements of micro- and nanospheres with diameters from 0.3 to 9.9 µm in 600 µl of 10 mM KCl. Nanospheres (5 µl, 10% solids) with diameter of 0.30 µm (triangles), 0.50 µm (circles), and 9.9 µm (squares) were placed in 600 µl of 1 mM KCl solution at pH 5.0. Impedance measurements were performed at temperatures ranging from 23.5° C. to 40.0° C. The CRF showed no significant dependence upon temperature over the range tested. Dielectric heating effects were not observed during measurements.

Test Samples Containing Nanospheres with Different Diameters

Figure 16A:
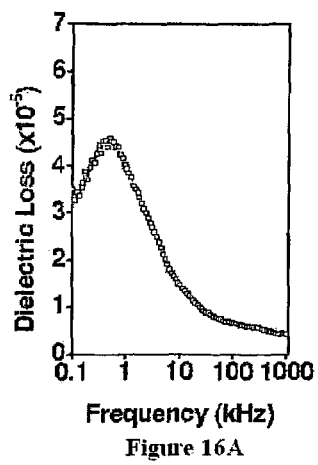
FIG. 16 is graphs of: (A) dielectric loss as a function of frequency for 5 µl (10% solids) of 0.30 µm diameter nanospheres in 1 mM KCl at pH 5.0; (B) dielectric loss as a function of frequency for 5 µl (10% solids) of 9.9 µm diameter microspheres in 1 mM KCl at pH 5.0; (C) corresponding data points from FIGS. 16A and 16B added together and divided by two and plotted versus frequency; (D) dielectric loss as a function of frequency for 2.5 µl (10% solids) of 0.30 µm diameter nanospheres plus 2.5 µl (10% solids) of 9.9 µm diameter microspheres in 600 µl 1 mM KCl at pH 5.0; and (E) the sum of two Gaussian distributions with centers at 486 Hz and 16.7 kHz.
Figure 16B:
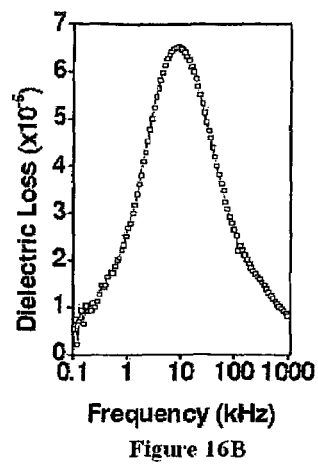
Figure 16C:
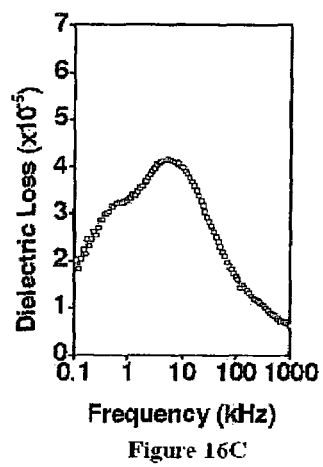
Figure 16D:
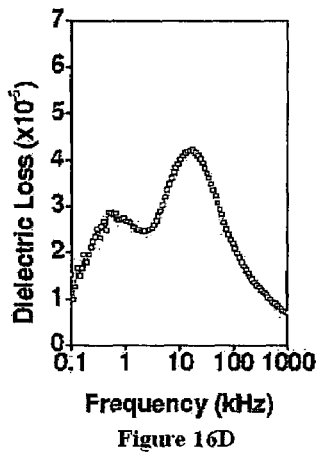

Dielectric relaxation spectra from solutions with 5 µl of 0.3 µm diameter nanospheres and 5 µl of 9.9 µm diameter microspheres are shown in FIGS. 16A and 16B, respectively. Summing FIGS. 16A and 16B and dividing by two (FIG. 16C) closely matches the response shown in FIG. 16D, which is a DRS response of a solution with 2.5 µl of 0.3 diameter nanospheres combined with 2.5 µl of 9.9 µm diameter microspheres in 600 µl of 10 mM KCl. In this case, individual concentrations of nanospheres were chosen so that the total number of nanospheres in solution remained the same in FIGS. 16A, 16B, and 16D.

Figure 16E:
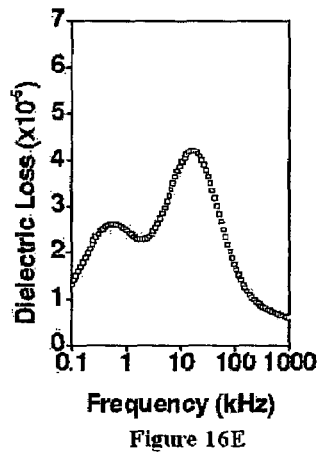

FIG. 16E shows the sum of two mathematically computed Gaussian distributions with centers at 486 Hz and 16.7 kHz. The profile of the Gaussian sum agrees closely with the data in FIG. 16C. The ability to separately resolve dielectric loss peaks corresponding to sized nanospheres opens the door to the possibility of dynamically tracking nanosphere populations in real-time with remote electrodes.

Discussion

In this Example, the removal of contact between electrodes and solutions under interrogation using DRS completely eliminates problems associated with interfacial polarization. This remote electrode approach also has significant advantages in special handling situations such as sensing hazardous materials (e.g. due to chemical toxicity or radioactivity) or when sensing is performed remotely to maintain functional aspects of the environment under interrogation.

In summary, ionic polarization of the counter ions surrounding micro- and nano-spheres can be used to sense particle distributions within solutions using remote electrodes.

By selecting the sizes of particles in different environments, it is possible to distinguish and separately track the presence of two or more particle species.

EXAMPLE 2

Real-Time Impedance Spectroscopy Biosensor with Remote Electrodes

Measurement of Dielectric Relaxation

The DRS apparatus of Example 1 was used to measure agglutination of functionally coated particles. In this study, no attempts were made to optimize design factors, such as minimum sample volumes or fluid exchange times.

Dielectric loss was calculated from impedance measurements of each sample using the equation:

$$\varepsilon''(\omega) = \left( \frac{d \cdot |Y| \cdot \cos(\phi)}{A \cdot \varepsilon_v \cdot \omega} \right) \quad \text{(eqn. 6)}$$

where $\varepsilon''$ is dielectric loss, d is the distance between electrode plates, Y is admittance, $\phi$ is the phase angle difference between the applied voltage and the measured response, A is the area of the electrode plates, $\varepsilon_v$ is the permittivity of free space ($8.854 \times 10^{-12}$ F/m) and $\omega$ is $2\pi$ times the applied frequency. Dielectric loss was plotted versus frequency on a log scale from 100 Hz to 1 MHz.

Before adding nanospheres, sweeps of bulk test solution were performed. These data were treated as background and subtracted from sweeps collected after nanospheres were added. Although measurements of dielectric loss over the selected frequency range in the absence of nanospheres contribute only a minor component compared to sweeps in the presence of nanospheres, this procedure reduces any effects due to stray capacitance or background dielectric effects.

Materials

Streptavidin-coated nanospheres were obtained from Bangs Labs (Fishers, Ind.). They were shipped as 0.8% solids in a buffer consisting of 100 mM borate, 0.01% BSA, 0.05% Tween 20 and 10 mM EDTA at pH 8.5, with a density of 1.06 gm/cm$^3$. All buffers were created using reagent-grade components obtained from Sigma-Aldrich.

Biotinylated bovine serum albumin (bBSA) from Vector Laboratories (Burlingame, Calif.), was reconstituted by adding 2 ml of deionized water to 10 mg of lyophilized protein. The bBSA stock solution contained 10 mM HEPES, 0.15 M NaCl and 0.08% azide at pH 7.5.

The streptavidin-biotin binding pair was chosen for its remarkably high binding affinity of $10^{15}$ M$^{-1}$ (approaching the binding affinity of a covalent bond), allowing study of agglutination effects without the need to account for kinetic effects. Biotinylated BSA was selected so that multiple biotin molecules would be available for binding to the streptavidin molecules on the surface of the nanospheres. The aim was for the streptavidin-coated nanospheres to form complexes (agglutinate), in the presence of bBSA.

Results

Unmodified Versus Biologically Modified Nanospheres

Figure 17:
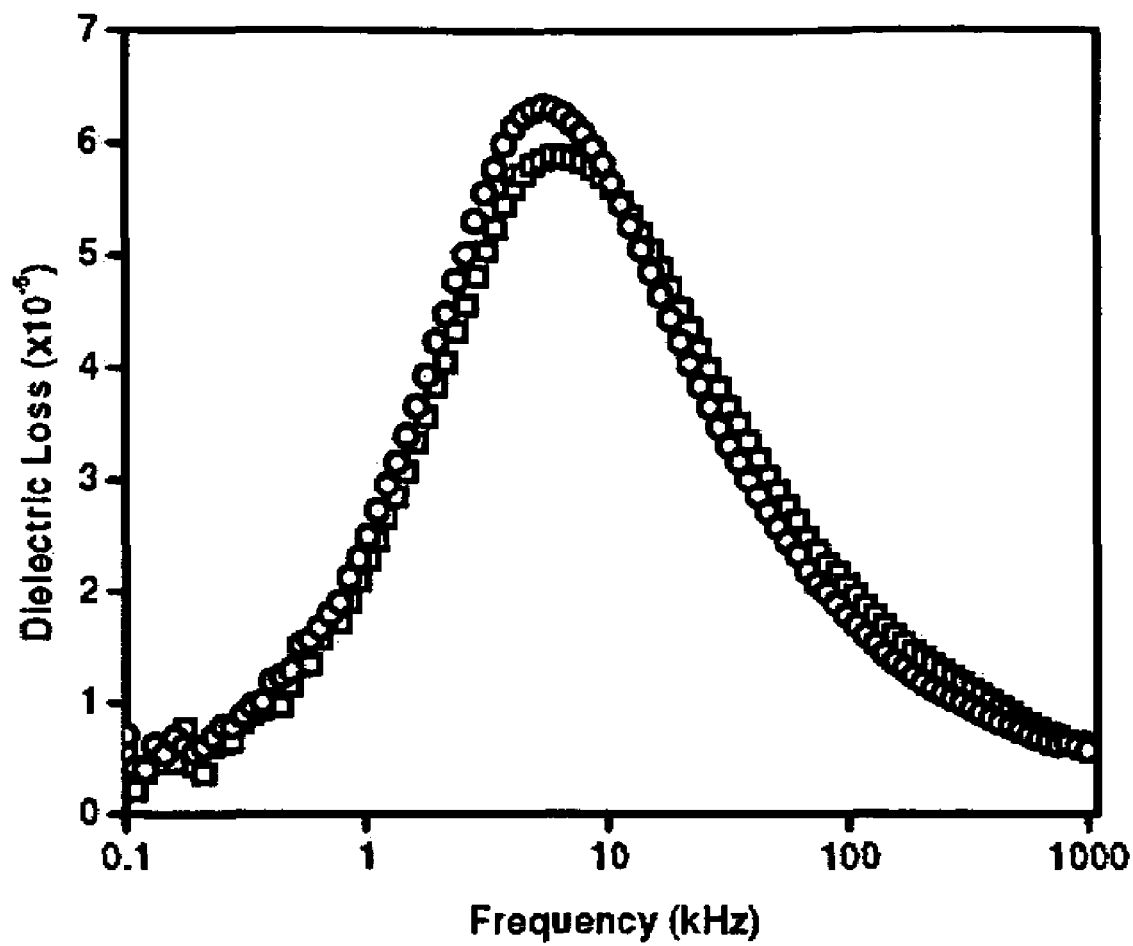
FIG. 17 is a graph of dielectric loss as a function of frequency for 5 µl (10% solids) of 0.53 µm diameter nanospheres coated with streptavidin (CRF=5462 Hz, circles) compared to unmodified 0.50 µm diameter nanospheres (CRF=5995 Hz, squares).

FIG. 17 compares the DRS response of uncoated nanospheres to streptavidin-coated nanospheres of nearly the same diameter. The unmodified nanospheres (0.50 μm diameter) have a measured characteristic relaxation frequency (CRF) of 5995 Hz. The streptavidin-modified nanospheres (0.53 μm diameter) have a CRF of 5462 Hz. The previously discussed relationship between particle size and CRF predicts that an increase in particle diameter of 0.03 μm should result in a CRF decrease of approximately 283 Hz. This places the size-corrected CRFs of the modified and unmodified spheres to within contiguous measurement points of the gain/phase analyzer. The remaining difference between CRFs is beyond the resolution of the instrument used in this study. Without being bound by theory, the change in particle diameter is believed to account for the frequency shift and no measurable effect was attributed to the streptavidin. However, streptavidin-coated nanospheres were shipped in 0.01% BSA and may have some adsorbed BSA even with the addition of Tween 20.

Particle Size and Environment Effects

The CRF of a solution exhibiting a-dispersion is determined by the size of the suspended particles, electrolyte concentration of the bulk solution, and pH. These parameters were used to compare dielectric loss in test solutions containing biologically modified nanospheres to plain, unmodified nanospheres.

Figure 18A:
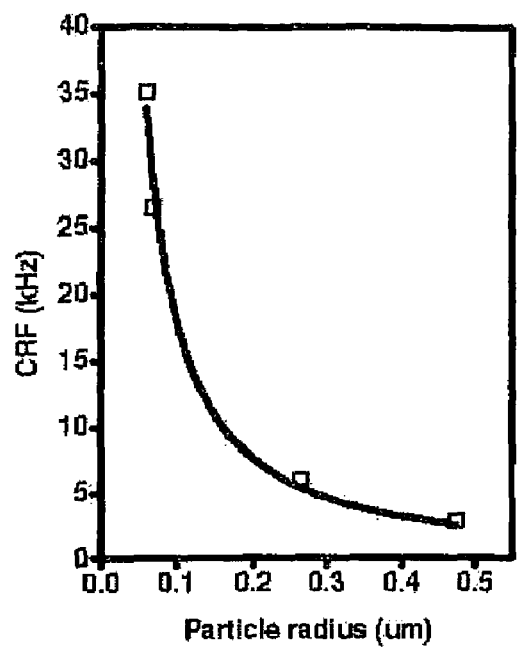
FIG. 18 is graphs of CRF as a function of particle size (A), electrolyte concentration (B), and pH (C).

FIG. 18A shows DRS responses of streptavidin-coated nanospheres with diameters ranging from 0.12 to 0.95 μm in 600 μl of 1.0 mM KCl at pH 5.0. CRFs were: 0.12 μm (35.1 kHz), 0.14 μm (26.6 kHz), 0.53 μm (6 kHz), and 0.95 μm (2.9 kHz). An equation of the form a~r$^b$ was used to curve-fit the CRFs where r represents particle radius. Least squares values for a and b were 1.0 kHz and −1.2, respectively.

These data are similar to results from experiments conducted using plain, unmodified nanospheres (FIG. 12). Both modified and unmodified nanosphere data sets differ slightly from the inverse square relation between CRF and particle size predicted by Schwarz, Phys. Chem., 66: 2636-2642, 1962.

Figure 18B:
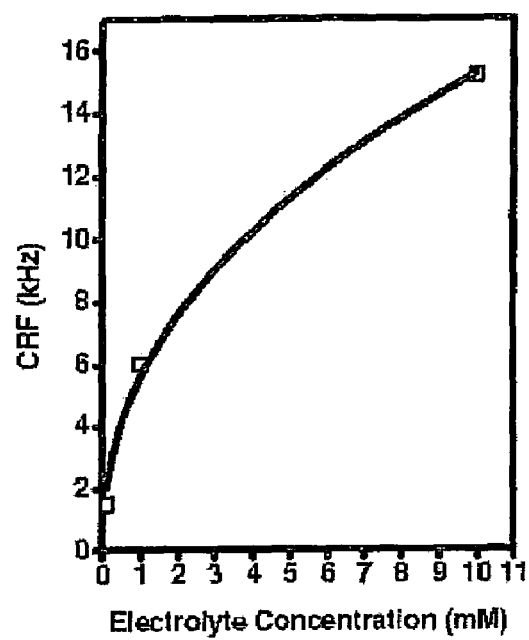

Again, without being bound by theory, as the electrolyte concentration of the test solution increases, the charge double layer is believed to compresses. This results in a shorter path length for counter ions surrounding the particles to follow when responding to an applied AC field. FIG. 18B illustrates how CRF changes as a function of electrolyte concentration for test solutions containing 0.53 μm diameter streptavidin-coated nanospheres at pH 5.0 in 600 μl of 0.1, 1, and 10 M KCl solutions. CRFs were: 0.1 mM KCl (1.5 kHz), 1.0 mM KCl (6.0kHz), and 10.0 mM KCl (15.2 kHz). As predicted, CRF frequencies increase with increasing analyte concentration. When CRF data are curve-fit to an equation of the form a·[K$^+$]$^b$, the optimum least-squares fit results in a power term, b, of 0.44 and a proportionality constant, a, of 5.6 kHz/mM. The parameters are identical to those measured in KCl solutions containing unmodified nanospheres.

Figure 18C:
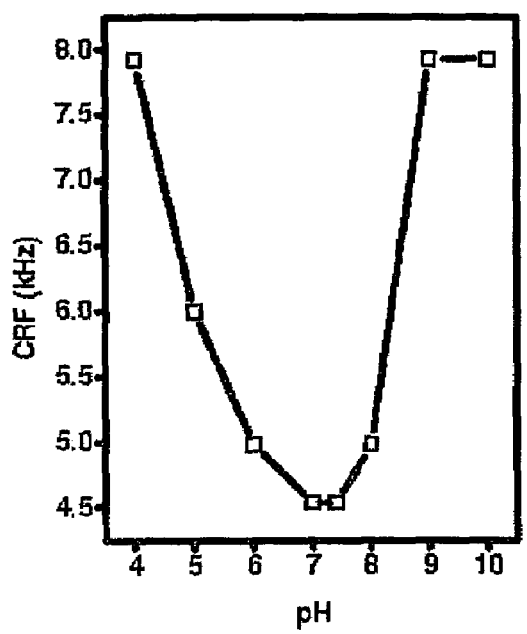

Without being bound by theory, at low pH, H$^+$ ions make up the bulk of the cloud of counter ions surrounding each particle. As shown in Example 1 for unmodified nanospheres (FIG. 14C), the CRF dips as the pH approaches neutrality. On the other hand, increasing pH beyond neutral causes the CRF to shift again to higher frequencies due to the increased ionic strength of the counter ions other than H$^+$ in solution. FIG. 18C shows the CRF dependence on the pH of test solutions ranging from pH 4.0 to 10.0 containing 0.53 μm diameter streptavidin-coated nanospheres in 600 μl of 1 mM KCl solution with K$^+$ as the dominant ion in solution. CRFs were: pH 4.0 (7.9 kHz), 5.0 (6.0 kHz), 6.0 (5.0 kHz), 7.0 (4.5 kHz), 7.4 (4.5 kHz), 8.0 (5.0 kHz), 9.0 (7.9 kHz), and 10.0 (7.9 kHz). The trace profile, including position and magnitude of minimum CRFs, is identical to unmodified nanospheres (FIG. 21C, below).

Particle Agglutination Effects

Figure 19:
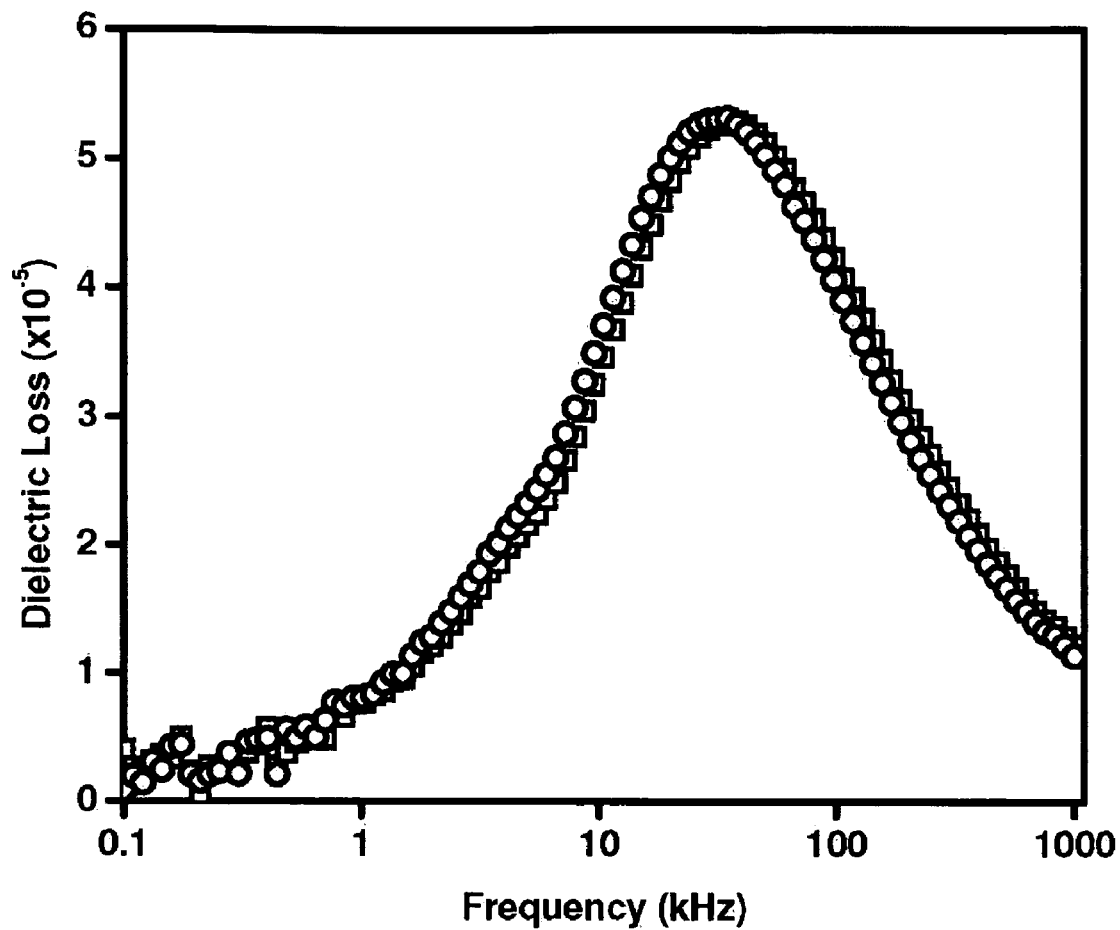
FIG. 19 is graph of dielectric loss versus frequency for a solution containing unmodified nanospheres.

As a negative control, high concentrations of bBSA were added to samples containing plain (non-streptavidin coated) nanospheres. The data in FIG. 19 were collected by adding 2 µl of $7.7 \times 10^{-5}$ M bBSA (0.8% solids) to 600 µl 1 mM KCl solution containing 2 µl of 0.12 µm diameter nanospheres. Prior to adding bBSA and throughout the observation period (18 minutes) the CRF remained at 35.1 kHz.

In order to measure the effect of agglutination on DRS responses, 2 µl (0.8% solids) of 0.12 µm diameter streptavidin-coated nanospheres were placed in 600 µl of 1 mM KCl. DRS measurements were performed just before adding bBSA (i.e. t=0) and at 3 minute intervals after the addition of various amounts of bBSA.

Figure 20A:
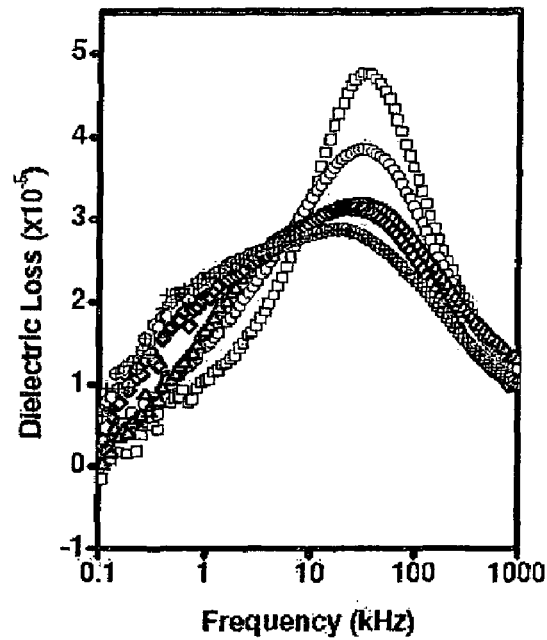
FIG. 20 is graphs of dielectric loss versus frequency for: (A) 600 µl 1 mM KCl test solution containing 2 µl (0.8% solids) of 0.12 µm diameter streptavidin-coated microspheres and $2.56 \times 10^{-10}$ M bBSA at t=0 min. (squares), t=3 min. (circles), t=6 min. (triangles), t=9 min (diamonds), 12 min (hexagons), and 15 min (pentagons); (B) same as A, but with $2.56 \times 10^{-8}$ M bBSA and an additional point at t=18 min (crosses); (C) same as B, but with $2.56 \times 10^{-7}$ M bBSA.

Agglutination due to the addition of $7.7 \times 10^{-8}$ M bBSA (i.e. final [bBSA]=$2.56 \times 10^{-10}$ M) yielded the results shown in FIG. 20A. The CRF of the 0.12 µm diameter streptavidin-coated nanospheres at t=0 minutes was 35.1 kHz. Beginning at t=3 minutes, a peak can be seen forming in the 2.0 kHz region. The amplitude of the nascent lower frequency peak (representing the newly forming bBSA/streptavidin-coated nanosphere complexes) continued to grow larger as the higher frequency peak (representing the free 0.12 µm diameter PS nanospheres) decreased in amplitude. Responses were monitored for up to 18 minutes, when a steady state was reached with no further significant changes in dielectric spectra.

Figure 20B:
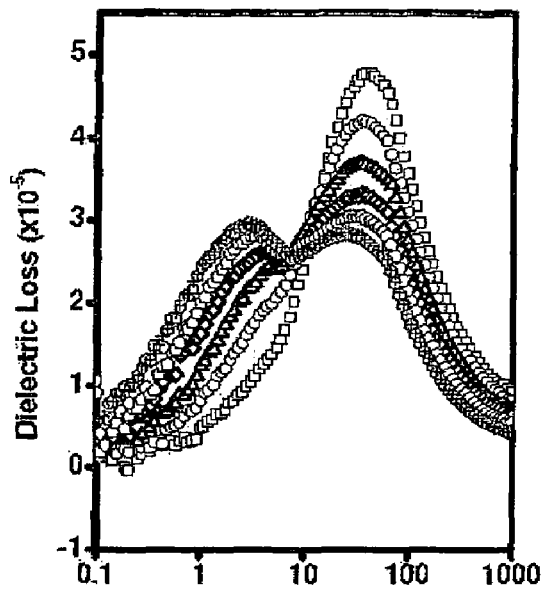
Figure 20C:
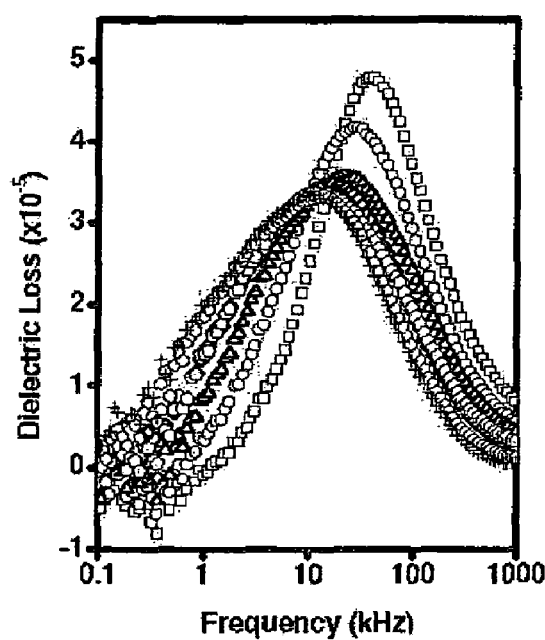

Increasing bBSA concentration 100-fold to $2.56 \times 10^{-8}$ M caused the nascent lower frequency peak at 2.0 kHz to develop more fully (FIG. 20B). Approximately equal dielectric loss peak amplitudes were observed at high and low frequencies at steady state when the bBSA concentration was further increased to $2.56 \times 10^{-7}$ M (FIG. 20C).

Size-Distribution of Agglutinated Clusters

Figure 21A:
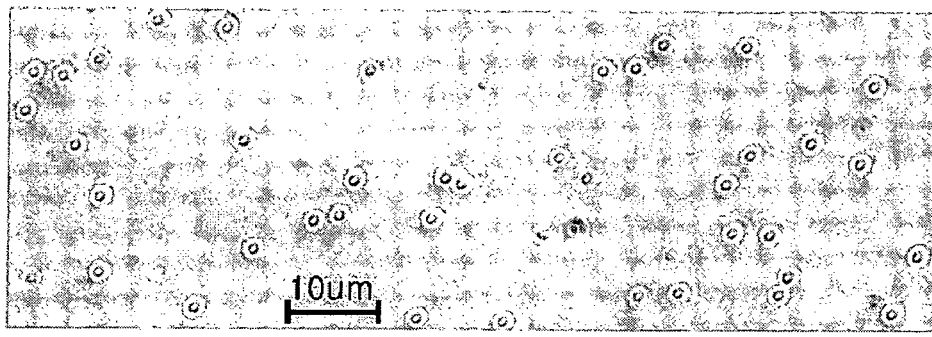
FIG. 21 is: (A) a photomicrograph of singlet 1.0 µm diameter plain (i.e. no streptavidin) nanospheres in a test solution containing excess ($1.28 \times 10^{-7}$ M) bBSA; (B) a photomicrograph of 0.95 µm diameter streptavidin-coated nanospheres in a test solution containing $1.28 \times 10^{-10}$ M bBSA; (C) a bar graph of the percent of total clusters for various clusters for various types of particles.
Figure 21B:
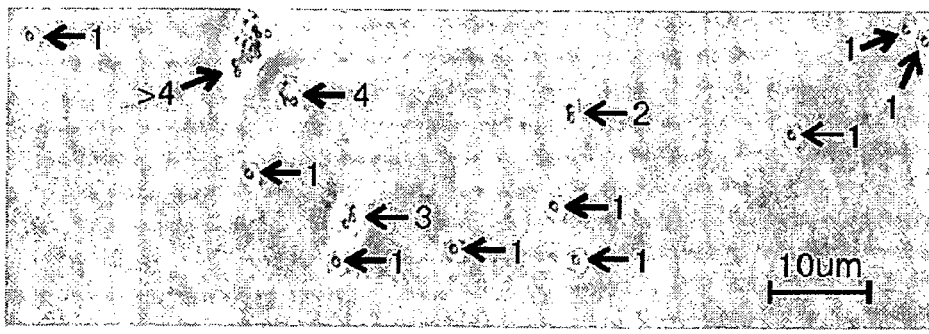
Figure 21C:
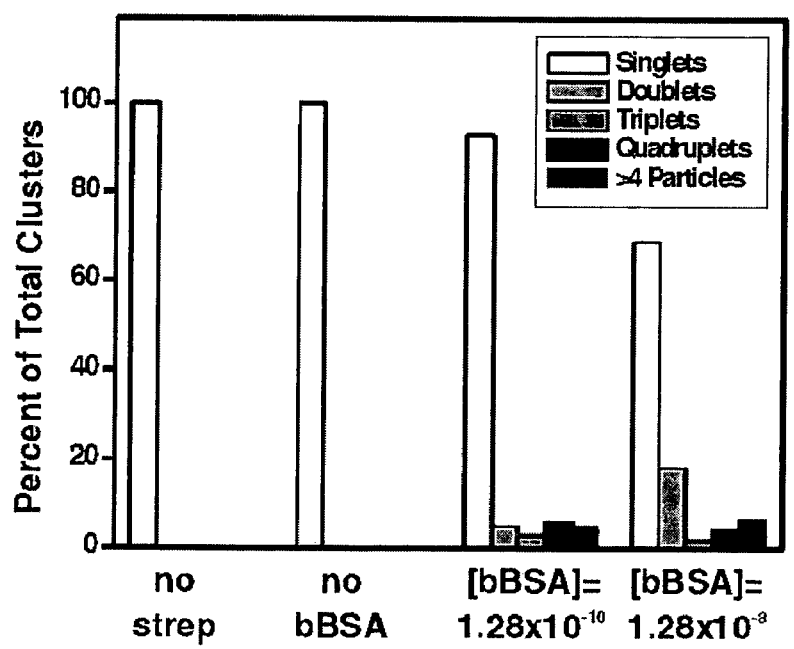

Test samples were examined visually using phase contrast microscopy (Nikon Eclipse E400) to determine the numbers of individual particles that make up clusters (FIG. 21). This was performed by pressing a cover slip over a drop (1 µl) of test solution and examining representative fields-of-view. Only singlets (mono-disperse particles) were seen when excess amounts ($7.7 \times 10^{-5}$ M) of bBSA were added to samples containing 5 µl (10% solids) of 1.0 Jm diameter, plain spheres in 600 µl of solution. A representative field-of-view of uniformly singlet complexes composed of unmodified spheres is shown in FIG. 21A. The numeric labels in FIGS. 21A and 21B correspond to identified singlets (1), doublets (2), triplets (3), quadruplets (4) and clusters containing >4 particles (>4). Similarly, when streptavidin-coated nanospheres were viewed in the absence of bBSA, only singlet particles were observed. These two conditions are shown as the left-most conditions in FIG. 21C.

When streptavidin-coated nanospheres were placed in the presence of bBSA, clusters containing 2 to >4 nanospheres were observed. FIG. 21B shows an example of a field-of-view of a test sample containing 1 µl of $7.7 \times 10^{-8}$ M bBSA added to 600 µl KCl solution containing 5 µl of 0.95 µm diameter (0.8% solids) nanospheres (i.e. [bBSA]=$1.28 \times 10^{-10}$). In this sample, the nanosphere population was composed of 69% singlets, 18% doublets, 2% triplets, 4% quadruplets, and 7 percent of clusters>4 particles. A test sample with $1.28 \times 10^{-10}$ M bBSA added to a test solution containing 0.95 µm diameter streptavidin-coated nanospheres had 93% singlets, 5% doublets, 3% triplets, 6% quadruplets, and 5% of clusters>4 particles. The rightmost conditions in FIG. 21C show a breakdown of complex distributions with bBSA present in solution. Higher concentrations of bBSA lead to fewer singlets and more complexes composed of larger numbers of particles.

Dynamics of Particle Agglutination

Figure 22A:
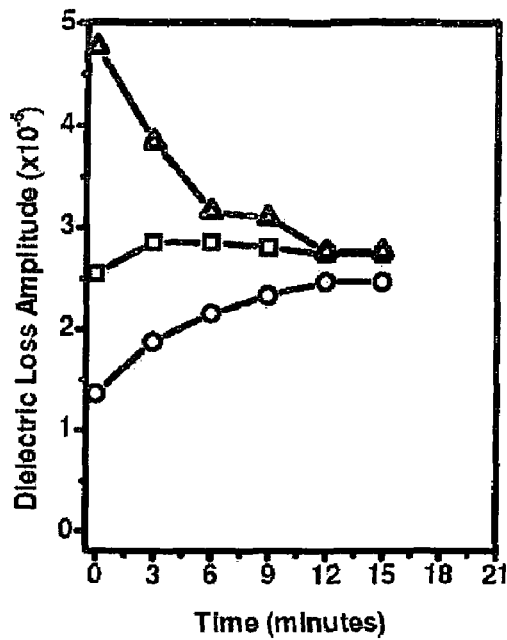
FIG. 22 is graphs of dielectric loss amplitudes versus time at 2.0 kHz (center of agglutinated responses, circles), 6.6 kHz (isosbestic frequency, squares), and 35.1 kHz (singlet CRF, triangles) based on data from: (A) FIG. 20A; (B) FIG. 20B; and (C) FIG. 20C.
Figure 22B:
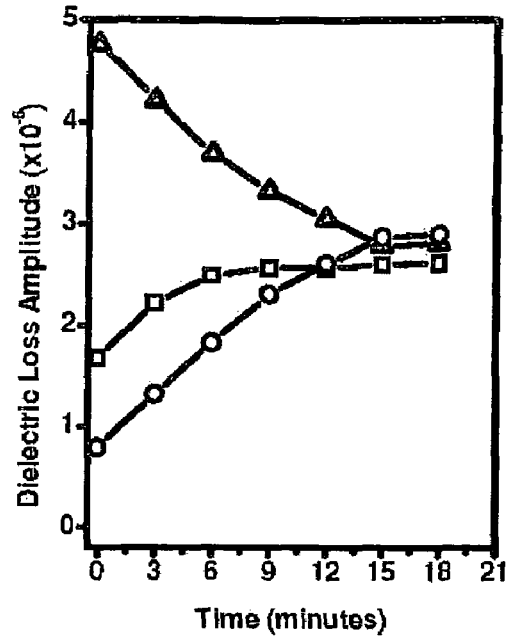
Figure 22C:
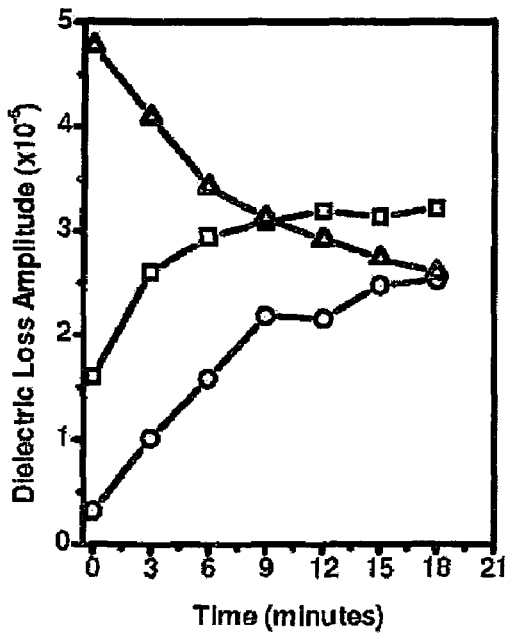

FIG. 22 shows the temporal progression of particle agglutination by monitoring the amplitudes of dielectric relaxation peaks associate with single particles (35.1 kHz, diamonds) and agglutinated complexes (2.0 kHz, circles). At all concentrations of bBSA, there is a progressive decrease in the DRS amplitude associated with singlets and an increase in the amplitude associated with multiple particle complexes. Steady state is achieved within 18 minutes. In addition, FIG. 22 shows the behavior of the equivalent of an isosbestic point (6.6 kHz, squares) where amplitudes are relatively stable in between two regions that vary in opposite directions. There is some movement of the isosbestic point, particularly early on during agglutination. The distribution of particle complexes that are formed (doublets, triplets, etc) and the fact that larger complexes "consume" more individual particles, decreasing the magnitude of the overall dielectric response contributes to the movement of the isosbestic point.

Figure 23:
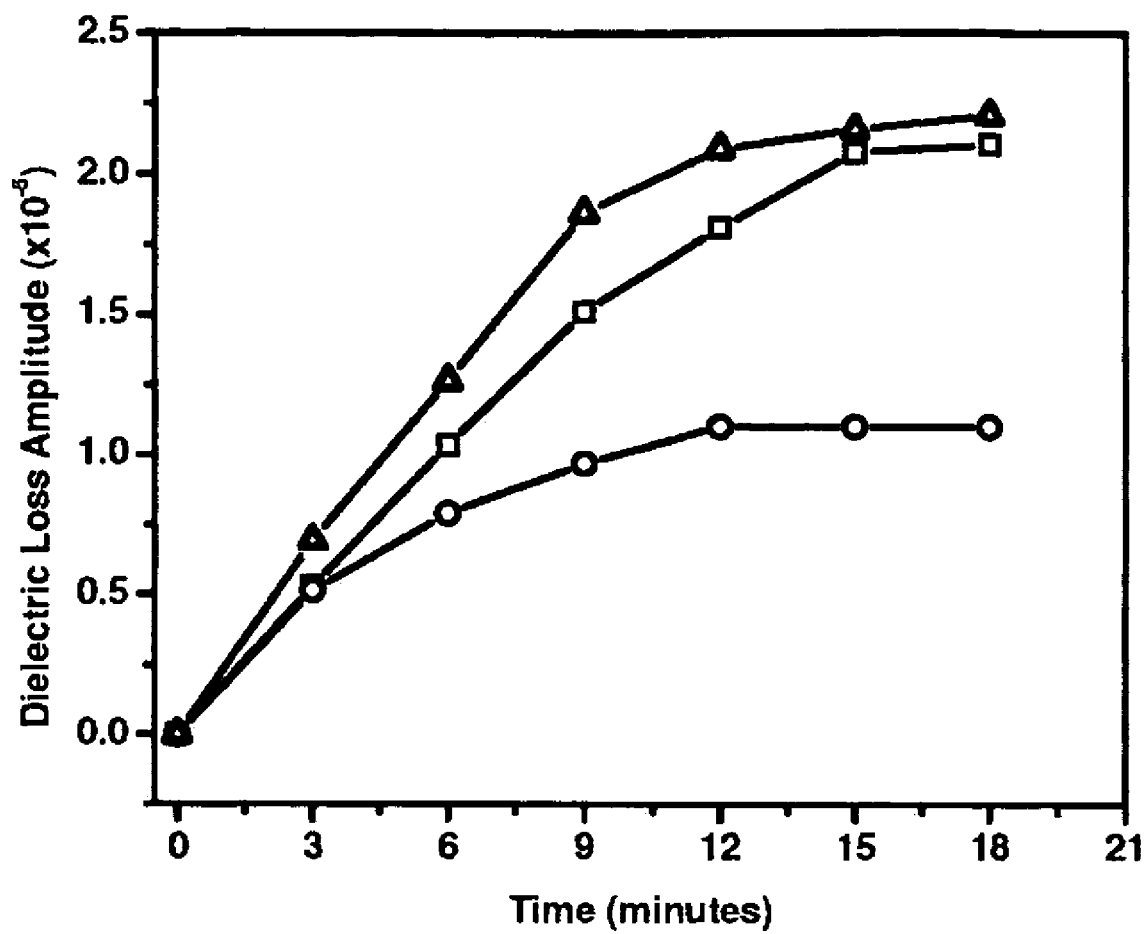
FIG. 23 is a graph of dielectric loss amplitudes at 2.0 kHz (agglutinated responses) versus time for test solutions containing 0.12 µm diameter streptavidin-coated nanospheres in KCl with $1.28 \times 10^{-10}$ bBSA (circles), $1.28 \times 10^{-8}$ bBSA (squares), and $1.28 \times 10^{-7}$ M bBSA (triangles).

FIG. 23 shows the amplitude of the peaks associated with agglutinated complexes (i.e. at 2.0 kHz) at different bBSA concentrations. Traces show that the rate of formation of the dielectric relaxation peak associated with agglutination increases with increasing concentrations of analyte. This rate dependence provides a method of estimating analyte concentration without the need for waiting until the system reaches steady state.

Discussion

In this study, agglutination was utilized to transform a system containing particles of one size and exhibiting a-dispersion as the primary dielectric relaxation mechanism, into a system with distributed populations of particle sizes. In Example 1, it was shown that test samples containing particles with two different diameters yield two discernable α-dispersion CRFs, one for each sized nanosphere in the sample (FIG. 16). Discrete population responses can be modeled as superimposed Gaussian distributions with distinguishable CRFs that are directly related to nanosphere size. Any chemistry that causes nanospheres to agglutinate results in solutions that, at any instant in time, contain a mix of free, mono-disperse particles and agglutinated complexes behaving as larger particles. This Example demonstrates that DRS using functionally coated particles can be used as a sensor, where streptavidin-coated nanosphere agglutination was induced by adding a test analyte, bBSA.

In the presence of analyte, the decrease in the dielectric relaxation peak associated with singlet nanospheres and the simultaneous development of a lower frequency dielectric component associated with agglutinated complexes provides a method to directly quantify the amount of analyte independent of factors such as the number of nanospheres present in the system. DRS responses contain the equivalent of an isosbestic point (6.6 kHz in FIG. 21A) where little change is observed. During agglutination at higher analyte concentrations, the DRS isosbestic point moves somewhat due to the formation of distributions of clusters, effectively removing a varying number of signal generators from measurements.

The DRS responses may be quantified by taking advantage of the typically proportional relation between analyte concentration and opposing changes in amplitude at different CRFs. In the symbols below, subscript a is utilized to represent agglutination and 1 to represent singlet. The magnitude of dielectric loss is typically proportional to the total number of particles, therefore, the contributions to the total amplitude measured at each CRF can be described using proportionality constants. A double subscript is utilized below where the first subscript represents the CRF at which measurements are taken and the second subscript represents the particle type (i.e. agglutinated or singlet) generating the response. The amplitude of the response at the agglutinated particle CRF, $A_a$, can be expressed as:

$$A_a = S_{aa} \cdot C_a + S_{a1} \cdot C_1 \tag{eqn. 7}$$

where $C_a$ is the concentration of agglutinated particles and $C_1$ is the concentration of singlet particles. If the amplitude of the response at the singlet particles CRF, $A_1$, has little or no component contributed by agglutinated particles (i.e. $S_{1a}=0$), then:

$$A_1 = S_{11} \cdot C_1 \tag{eqn. 8}$$

This assumption is true both when no analyte, and therefore no agglutinated particles, are present, as well as when saturating amounts of analyte are present and all particles agglutinate into one large mass. At intermediate values, the contribution is minimal if there is sufficient separation between the agglutinated and single particle CRFs (FIG. 24).

Figure 24:
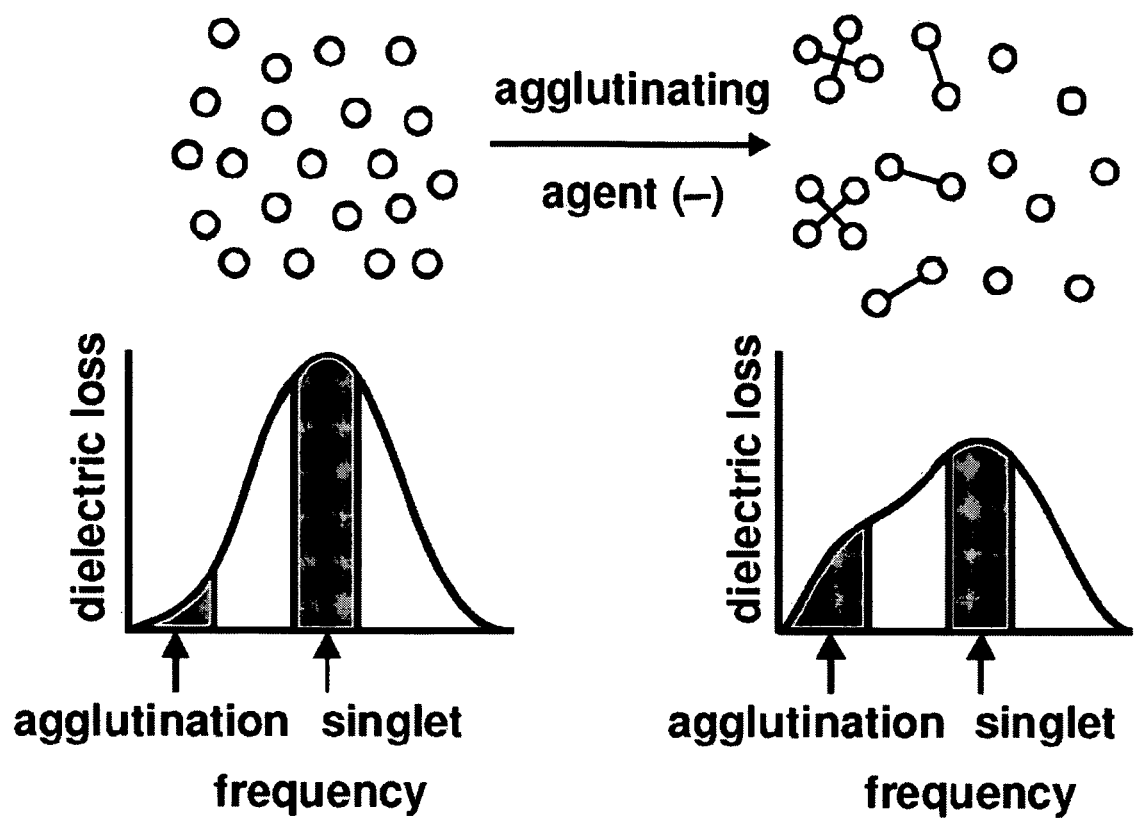
FIG. 24 is a schematic diagram of how mono-disperse particles result in a single Gaussian distribution DRS response with a large amplitude CRF (left side) and how agglutinated clusters of particles cause the formation of a distributed response at lower frequencies and removal of singlets that contribute to the higher CRF response (right side.)

Without being bound by theory, FIG. 24 presents a schematic diagram of how mono-disperse particles may result in a single Gaussian distribution DRS response with a large amplitude CRF (left side) and how agglutinated clusters of particles may cause the formation of a distributed response at lower frequencies and may remove singlets that contribute to the higher CRF response (right side.) In FIG. 24, arrows indicate the positions of the singlet CRF (rightmost arrow in each panel) and peak of the agglutinated response (leftmost arrow in each panel). Shaded regions under the traces represent areas used to improve the ratiometric estimate of analyte concentration.

If a ratio, R, is defined as the amplitude measured at the agglutination frequency divided by the amplitude at the singlet frequency, then:

$$\frac{A_a}{A_1} \equiv R = \frac{S_{aa} \cdot C_a + S_{a1} \cdot C_1}{S_{11} \cdot C_1} \tag{eqn. 9}$$

The ratio eliminates the effects of scaling terms embedded within the amplitudes associated with the DRS apparatus and factors such as the total number of nanospheres present in solution, since these appear in both the numerator and denominator, canceling each other. The number of agglutinated particles is proportional to analyte concentration, [A], according to:

$$C_a = [A] \cdot C_1 / K_1 \tag{eqn. 10}$$

where $K_1$ is a constant that includes factors such as the dissociation constant for agglutination and the average number of particles that agglutinate into a cluster. Substituting equation 10 into equation 11 results in:

$$R = \frac{S_{aa} \cdot [A]}{S_{11} \cdot K_1} + \frac{S_{a1}}{S_{11}} \tag{eqn. 11}$$

where $S_{a1}/S_{11}$ can be recognized as the ratio of amplitudes with no analyte present and defined as $R_{min}$. Re-arranging equation 11 results in:

$$\frac{S_{aa} \cdot [A]}{S_{11} \cdot K_1} = R - R_{min} \tag{eqn. 12}$$

Finally, all of the terms $S_{aa}$, $S_{11}$ and $K_1$ can be recognized as being a constant factor and combined to form a single constant, K, resulting in:

$$[A] = K \cdot (R - R_{min}) \tag{eqn. 13}$$

Figure 25:
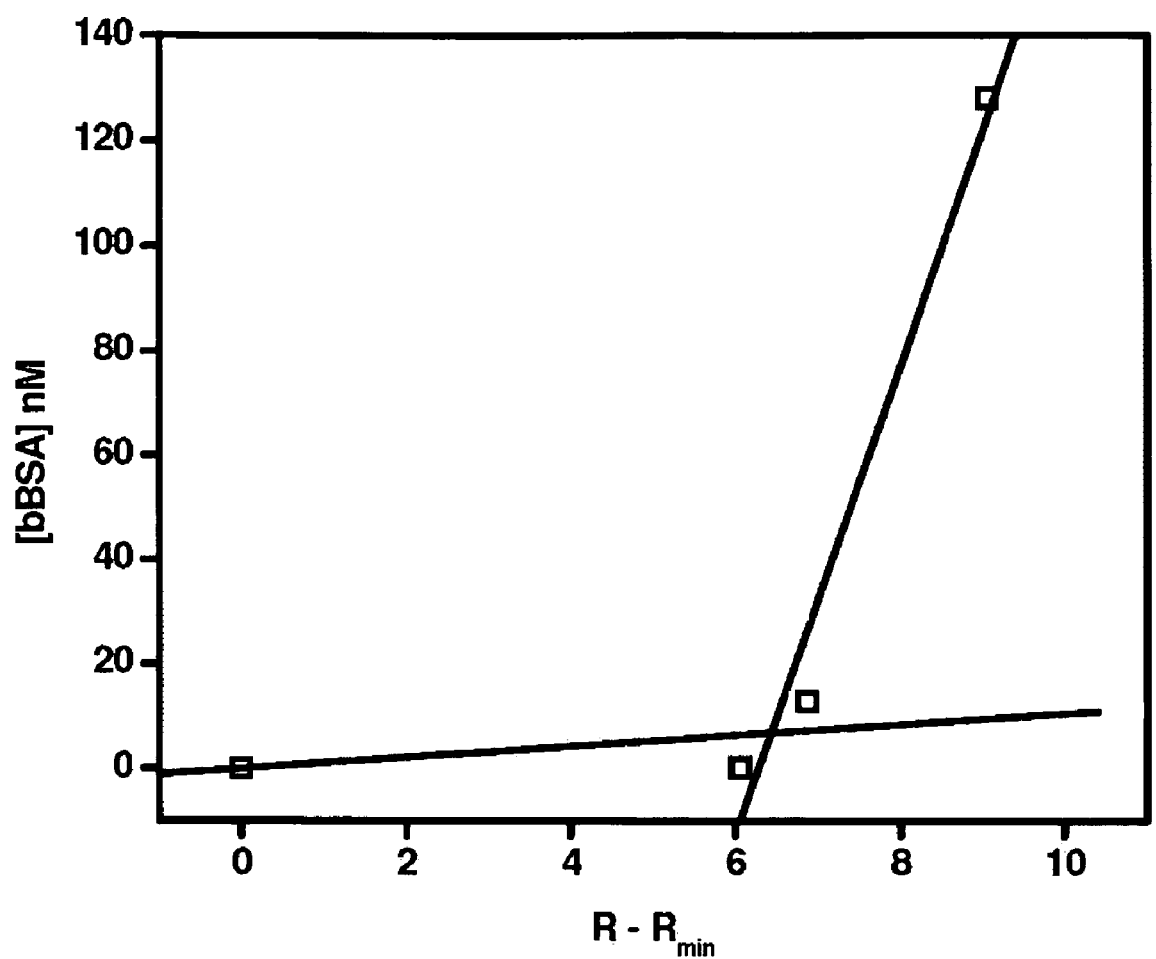
FIG. 25 is a graph of [bBSA] as a function of $(R-R_{min})$.

Constant K can then be determined empirically from standard curves such as shown in FIG. 25.

Nonlinearity due to high analyte concentration was seen in the standard curve in FIG. 25. At low concentrations the slope, K, was 10.6 nM. At higher concentrations the slope of the relation increased to K≈448 nM, likely due to the formation of large, multiple-particle complexes. This study did not use concentrations near the lower concentration limit of the employed DRS biosensor, as the lowest bBSA concentration was $1.28 \times 10^{-10}$ M. To determine the sensitivity of the DRS biosensor, and find the linear portion of the standard curve, R–Rmin data from experiments using bBSA concentrations below $1.28 \times 10^{-10}$ M should be added to the standard curve in FIG. 25.

An improvement in accuracy can be achieved over measurements of single-point, peak amplitudes by considering the area under regions centered on the agglutination and singlet CRFs. This arises because, as illustrated in FIG. 21, agglutination can generate an assorted population of agglutinated clusters consisting of doublets, triplets, and so on. Although low-number complexes contribute to the overall agglutination response, the distribution of agglutinated particles broadens the (non-Debye) response (i.e. lowering peak amplitude). By considering areas around the agglutination CRF, the range of agglutinated particles can be taken into account and the effects of "noise" within a single-measure, peak amplitude can be reduced. Using these techniques a constant of 3.6 nM was determined for sensing bBSA using streptavidin-coated spheres and considering 10 points on either side of the agglutination CRF and 3 points on either side of the singlet CRF.

A further refinement can be included if the size distribution of agglutinated complexes (i.e. number of particles making up each complex) is known. This arises because clusters consisting of a large number of particles indicate increased agglutination (i.e. increased analyte concentration) but are only counted as a single source of dipole relaxation at lower frequencies. This effect can be included by weighting lower frequency contributions to the agglutinated area higher than higher frequency components. This procedure has not been performed in the present studies but should provide a correction at high analyte concentrations.

The most sensitive measurements of concentration of the unknown species can be made once steady-state conditions have been achieved. However, the slopes or initial "velocity" of the progress curves (FIG. 22) can also be utilized as an early indicator of the final concentration of analyte. By choosing the affinities between the analyte and activated nanospheres, it is possible to fine-tune responsiveness versus steady-state sensitivity of the system. The system can also be setup in a competitive mode, were analyte is used to compete for self-agglutinating binding sites on nanoparticle surfaces.

In summary, DRS with remote electrodes provides a method to quantitatively and non-invasively interrogate solutions within enclosed tubes or chambers. The system is capable of continuous, real-time measurements under flow-through or stationary conditions. Since reactive components are isolated to solid surfaces, it is convenient to replenish a sensor or even switch sensed analyte by introducing fresh aliquots of particles. These attributes lead to a number of medical, agricultural, industrial and military applications.

It is to be understood that the detailed description of preferred and other embodiments is not to itself limit the scope of the invention.

We claim:

1. A dielectric relaxation spectroscopy apparatus comprising:
   (A) at least two electrodes;
   (B) an alternating current source in electrical communication with at least one of the electrodes;
   (C) a sample cell intermediate the electrodes and having at least one cell barrier section intermediate each of the electrodes and a sample containment section within the sample cell, wherein the cell barrier section is at least partially made from an electrical insulator, whereby the electrodes act as a capacitor with the sample cell forming a dielectric between the electrodes;
   (D) a plurality of discrete particles having a mean cross sectional width between about 0.01 μm and about 10 μm, whereby the interaction of a sample analyte and the particles produces a characteristic relaxation frequency in the range of about 400 Hz and about 200 kHz; and
   (E) a detector coupled to at least one of the electrodes and configured to measure characteristic relaxation frequencies in the range of about 400 Hz and about 200 kHz.

2. The dielectric relaxation spectroscopy apparatus of claim 1, wherein the particles are coated with an analyte binding substance.

3. A method of measuring an electrical property of a sample comprising:
   providing a liquid sample comprising an analyte;
   placing the sample between a plurality of electrodes in a sample cell comprising a sample cell barrier separating the sample from each of the plurality of electrodes;
   mixing a plurality of particles having a mean cross sectional width between about 0.01 μm and about 10 μm with the sample, the particles having a relaxation property;
   passing an alternating current through at least one of the plurality of electrodes; and
   measuring the relaxation property of the particles at a frequency between about 400 Hz and about 200 kHz.

4. The method of claim 3, wherein the relaxation property of the particles comprises a characteristic relaxation frequency and the sample comprises counter ions that interact with and modify the characteristic relaxation frequency of the particles.

5. The method of claim 3, wherein the relaxation property of the particles comprises a characteristic relaxation frequency, farther comprising adding counter ions to the sample, the counter ions being selected to interact with and modify the characteristic relaxation frequency of the particles.

6. The method of claim 3, wherein the particles are coated with a binding agent selected to bind the analyte.

7. The method of claim 3, wherein measuring the relaxation property comprises measuring the relaxation property of the particles before and after mixing the particles with the sample.

8. The method of claim 3, wherein the analyte forms a counter ion cloud around the particles.

9. The method of claim 3, wherein the particles and the analyte are oppositely charged.

10. The method of claim 3, wherein mixing a plurality of particles with the sample comprises mixing particles of a first size and particles of a second size with the sample, the analyte is a first analyte and the sample comprises a second analyte, and the particles of the first size are selected to preferentially interact with the first analyte.

11. The method of claim 10, wherein the particles of the second size are selected to preferentially interact with the second analyte.

12. The method of claim 10, wherein the particles of the first size are coated with a coating selected to preferentially bind the first analyte.

13. The method of claim 12, wherein the particles of the second size are coated with a coating selected to preferentially bind the second analyte.

14. The method of claim 3, wherein determining a relaxation property of the particles comprises determining the characteristic relaxation frequency of the interaction of the analyte and the particles, farther comprising determining a desired range for the characteristic relaxation frequency and selecting particles having a size selected such that the interaction of the analyte and the particles produces a characteristic relaxation frequency in a desired portion of a range between about 400 Hz and about 200 kHz that allows detection of the analyte.

15. The method of claim 3, wherein the particles bind to the analyte and measuring a relaxation property of the particles comprises monitoring a characteristic relaxation frequency of bound and unbound particles.

16. The method of claim 3, further comprising mixing a competing binding agent with the sample and wherein measuring a relaxation property of the particles comprises measuring the characteristic relaxation frequency of particles bound to the analyte and the characteristic relaxation frequency of particles bound to the competing binding agent.

17. The method of claim 3, wherein the particles agglutinate in the presence of the analyte, further comprising determining the analyte concentration at least substantially according to the formula:

$$[A] = K \cdot (R - R_{min})$$

wherein [A] is the analyte concentration, K is a constant, R is the ratio in the presence of a sample of the amplitude at a characteristic relaxation frequency of agglutinated particles to the amplitude at a characteristic relaxation frequency of unagglutinated particles; and $R_{min}$ is the ratio in the absence of analyte of the amplitude at a characteristic relaxation frequency of agglutinated particles to the amplitude at a characteristic relaxation frequency of unagglutinated particles.

18. A method of measuring an electrical property of a sample comprising:
   providing a liquid sample comprising particles having a mean cross sectional width between about 0.01 μm and about 10 μm and a characteristic relaxation frequency;
   placing the sample between a plurality of electrodes in a sample cell comprising a sample cell barrier separating the sample from each of the plurality of electrodes;
   passing an alternating current through at least one of the electrodes; and
   measuring the characteristic relaxation frequency of the particles at a frequency between about 400 Hz and about 200 kHz.

* * * * *